(12) United States Patent
Zhang et al.

(10) Patent No.: US 8,957,087 B2
(45) Date of Patent: Feb. 17, 2015

(54) HETEROCYCLIC SUBSTITUTED ACARDITE DERIVATE AND APPLICATION THEREOF

(75) Inventors: Aihua Zhang, Jiangsu (CN); Shengtao Yuan, Jiangsu (CN); Guang Cheng, Jiangsu (CN); Yipeng Shen, Jiangsu (CN); Ancheng Ji, Jiangsu (CN)

(73) Assignees: Jiangsu Provincial Institute of Materia Medica Co., Ltd., Nanjing, Jiangsu (CN); Nanjing Luyesike Pharmaceutical Co., Ltd., Nanjing, Jiangsu (CN)

( * ) Notice: Subject to any disclaimer, the term of this patent is extended or adjusted under 35 U.S.C. 154(b) by 404 days.

(21) Appl. No.: 13/318,904

(22) PCT Filed: May 4, 2010

(86) PCT No.: PCT/CN2010/072417
§ 371 (c)(1),
(2), (4) Date: Nov. 4, 2011

(87) PCT Pub. No.: WO2010/127608
PCT Pub. Date: Nov. 11, 2010

(65) Prior Publication Data
US 2012/0053192 A1    Mar. 1, 2012

(30) Foreign Application Priority Data

May 5, 2009    (CN) .......................... 2009 1 0026748

(51) Int. Cl.
| A01N 43/42 | (2006.01) |
| A61K 31/44 | (2006.01) |
| A01N 43/54 | (2006.01) |
| A61K 31/517 | (2006.01) |
| A61K 31/47 | (2006.01) |
| C07D 239/72 | (2006.01) |
| C07D 217/22 | (2006.01) |
| C07D 207/00 | (2006.01) |
| C07D 207/36 | (2006.01) |
| C07D 215/22 | (2006.01) |
| C07D 215/48 | (2006.01) |
| C07D 217/24 | (2006.01) |
| C07D 217/26 | (2006.01) |
| C07D 239/52 | (2006.01) |
| C07D 239/88 | (2006.01) |
| C07D 239/90 | (2006.01) |

(52) U.S. Cl.
CPC ............ *C07D 207/36* (2013.01); *C07D 215/22* (2013.01); *C07D 215/48* (2013.01); *C07D 217/24* (2013.01); *C07D 217/26* (2013.01); *C07D 239/52* (2013.01); *C07D 239/88* (2013.01); *C07D 239/90* (2013.01)
USPC ........ 514/300; 514/266.3; 514/309; 544/287; 546/141; 548/556

(58) Field of Classification Search
USPC ........ 514/300, 266.3, 309; 546/141; 544/287; 548/556
See application file for complete search history.

(56) References Cited

FOREIGN PATENT DOCUMENTS

WO    PCT/CN2010/072417    8/2010

OTHER PUBLICATIONS

Kubo et al. J. Med. Chem. 2005, vol. 48, pp. 1359-1366.*
NPL of EP 0 860 433 A1, 1998, pp. 1-125.*

* cited by examiner

*Primary Examiner* — Samira Jean-Louis
(74) *Attorney, Agent, or Firm* — Tianhua Gu; Global IP Services

(57) ABSTRACT

This present invention discloses a heterocyclic substituted acardite derivate and application thereof, namely compounds in the general formula (1) or the general formula (2) or pharmaceutically acceptable salts thereof, wherein A is monosubstituted or polysubstituted quinoline, isoquinoline, quinazoline, pyrrole or pyrimidine, and the substituent is halogen, $C_{1-5}$alkyl, $C_{1-5}$haloalkyl, $C_{1-5}$alkoxy, $C_{1-5}$haloalkoxy, $C_{1-5}$alkylamino, $C_{1-5}$haloalkylamino, amino or nitryl; $R_1$ is $C_{1-5}$alkyl; $R_2$ is one or more selected from hydrogen, halogen, alkyl, alkoxy, haloalkyl or haloalkoxy; and $R_3$ is one or more selected from hydrogen, halogen, alkyl, alkoxy, haloalkyl or haloalkoxy. The compound of the present invention and the pharmaceutically acceptable salt thereof can be used for treating tumor or leukemia.

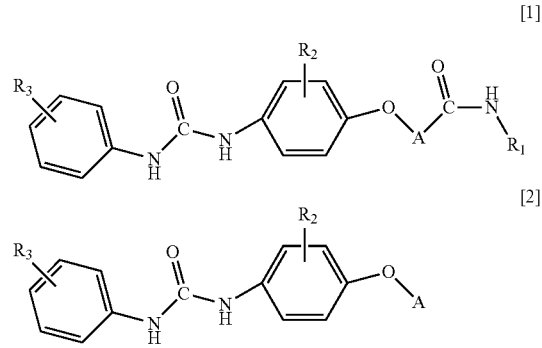

10 Claims, No Drawings

HETEROCYCLIC SUBSTITUTED ACARDITE DERIVATE AND APPLICATION THEREOF

Cross Reference to Related Patent Application

The present application is the US national stage of PCT/CN2010/072417 filed on May 4, 2010, which claims the priority of the Chinese patent application No. 200910026748.8 filed on May 5, 2009, which application is incorporated herein by reference.

FIELD OF THE INVENTION

This present invention relates to an aromatic heterocyclic substituted acardite derivate and application thereof In addition, the present invention relates to application of aromatic heterocyclic substituted acardite derivate and pharmaceutically acceptable salts thereof in the treatment of tumor or leukemia.

BACKGROUND OF THE INVENTION

With better understanding of the tumor molecular mechanisms, the research on the targeted therapy of the tumor moleculars has achieved important advance. Protein kinase inhibitor is one of newly developed targeted therapy drugs, which affects the survival, proliferation and disease progression of tumor cells through blocking the intra-cellular molecular transduction pathway. Raf kinases play a crucial role in the signal transduction pathway of Raf/MEK/ERK. Although the function of the Raf kinase in normal tissues is not yet understood, but the existing basic and clinical research results have shown that the upregulation of Raf gene and overexpression of its protein are present in various solid tumors, including renal cell carcinoma, hepatocellular carcinoma, melanoma and non-small cell lung cancer. Currently, more and more single target point and multi-target point therapy drugs for Raf kinases are successfully developed and applied clinically, for example, sorafenib and erlotinib have achieved good clinical results, and the anti-tumor therapy has came into the "molecular targeted therapy" era. CN200810129360.6 disclosed that a kind of aromatic heterocyclic substituted acardite derivates with no substituent or only carbamyl in the A ring have prospect of inhibiting specific tumors, and the preliminary pharmacological experiments found that the effects of some compouns are better than sorafenib.

SUMMARY OF THE INVENTION

The objective of the present invention is to provide an aromatic heterocyclic substituted acardite derivate having more medicinal value through structural modification based on the existing technology. After the present invention adds specific substituents in the A ring, especially adding substituents in the quinazoline, pyrrole or pyrimidine rings, the inhibitory activity and selectivity of the compounds to specific tumors are greatly increased, and the absorptivity and utilization rate of the compounds are increased and the toxic side effects are reduced. The objective of the present invention is further to provide application of the compound or pharmaceutically acceptable salts thereof in the treatment of tumor or leukemia. The heterocyclic substituted acardite derivate of the present invention can be represented by the following formulas [1] and [2]:

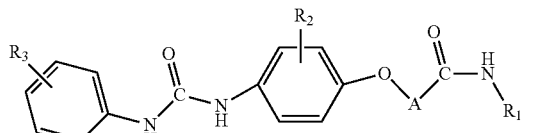

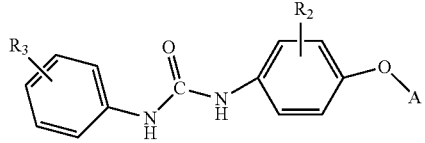

wherein,

A is monosubstituted or polysubstituted quinoline, isoquinoline, quinazoline, pyrrole or pyrimidine, preferably monosubstituted or polysubstituted quinazoline, pyrrole or pyrimidine, further preferably monosubstituted or polysubstituted quinazoline; the substituent is halogen, alkyl, haloalkyl, alkoxy, haloalkoxy, alkylamino, haloalkylamino, amino or nitryl, preferably halogen, $C_{1-5}$alkyl, $C_{1-5}$haloalkyl, $C_{1-5}$alkoxy, $C_{1-5}$haloalkoxy, $C_{1-5}$alkylamino, $C_{1-5}$haloalkylamino, amino or nitryl, more preferably halogen, $C_{1-5}$alkyl, $C_{1-5}$haloalkyl, $C_{1-5}$alkoxy, $C_{1-5}$haloalkoxy, amino or nitryl; still more preferably halogen, amino, $C_{1-5}$alkyl or $C_{1-3}$alkoxy, particularly preferably Cl, Br, F, amino, methoxy, methyl, ethyl, propyl, isopropyl, butyl or t-butyl in the present invention.

$R_1$ is alkyl, more preferably $C_{1-5}$alkyl, most preferably methyl, ethyl, propyl and isopropyl.

$R_2$ is one or more selected from hydrogen, halogen, alkyl, alkoxy, haloalkyl or haloalkoxy; preferably one or more selected from hydrogen, halogen, $C_{1-5}$alkyl, $C_{1-5}$alkoxy, $C_{1-5}$haloalkyl or $C_{1-5}$haloalkoxy, most preferably one or more selected from H, Cl, Br, F, methoxy, ethoxy, propoxy, methyl, ethyl, propyl, isopropyl, butyl, t-butyl or trifluoromethyl.

$R_3$ is one or more selected from hydrogen, halogen, alkyl, alkoxy, $C_{1-5}$ haloalkyl or $C_{1-5}$haloalkoxy, preferably one or more selected from hydrogen, halogen, $C_{1-5}$alkyl, $C_{1-5}$alkoxy, $C_{1-5}$haloalkyl or $C_{1-5}$haloalkoxy, most preferably one or more selected from H, Cl, Br, F, methoxy, ethoxy, propoxy, methyl, ethyl, propyl, isopropyl, butyl, t-butyl or trifluoromethyl.

The pharmaceutically acceptable salts of the compound in the present invention are selected from:
a) basic salts of inorganic acids and organic acids, the described acid is selected from hydrochloric acid, hydrobromic acid, sulfuric acid, phosphoric acid, mesylate, trifluoromethanesulfonic acid, benzene sulfonic acid, para-toluenesulfonic acid, 1-naphthalene sulfonic acid, 2-naphthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid or almonds acid;
b) acid salts of organic and inorganic base, the described cation is selected from alkali metal cation, alkaline earth metal cation, ammonium cation, aliphatic-substituted ammonium cation or aromatic-substituted ammonium cation.

Preparation of the Compound of Formula 1

Method 1: the target compound is obtained from substituted heterocyclic 2-carboxylate as starting materials through acyl chlorination, aminoalkylation, two-step condensation and salt forming reaction and the route is as follows:

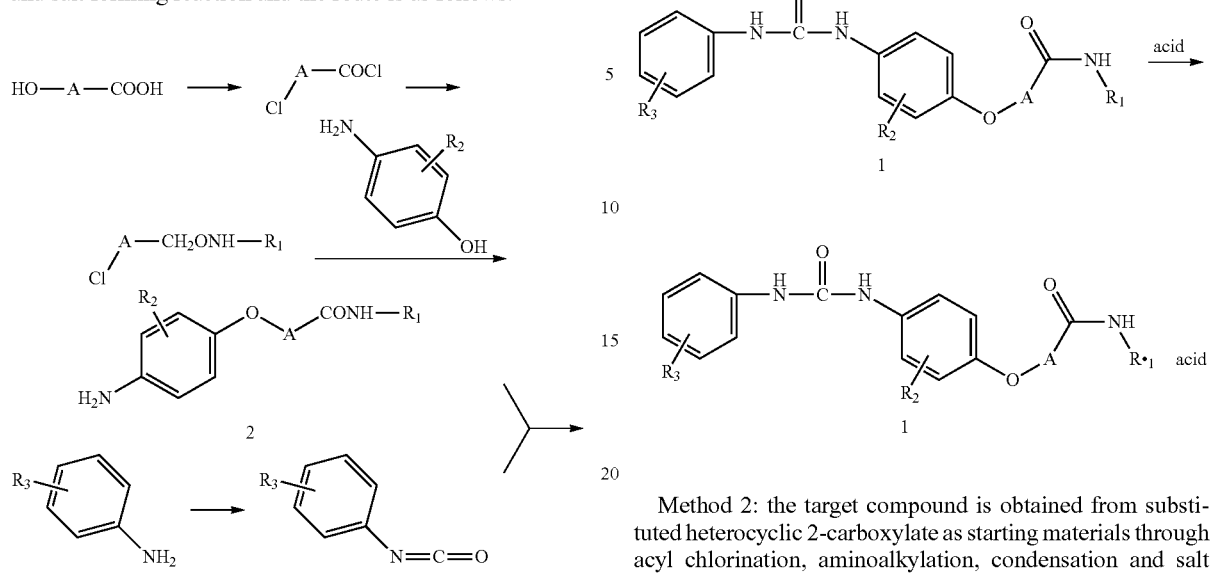

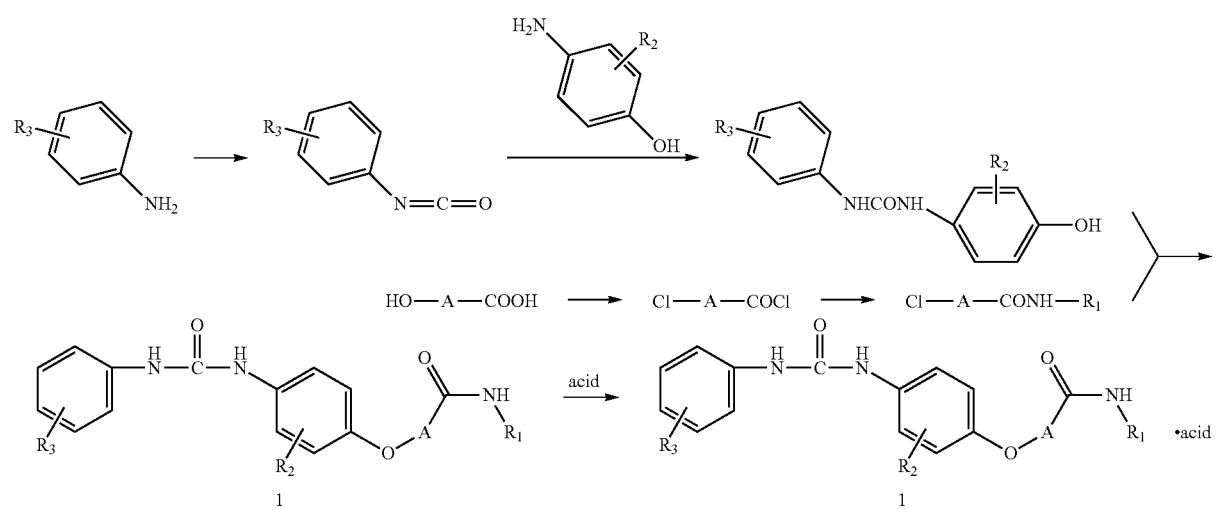

Method 2: the target compound is obtained from substituted heterocyclic 2-carboxylate as starting materials through acyl chlorination, aminoalkylation, condensation and salt forming reaction and the route is as follows:

Preparation of the Compound of Formula 2

The target compound is obtained from halogen substituted heterocyclic as starting materials through two-step condensation and salt forming reaction and the route is as follows:

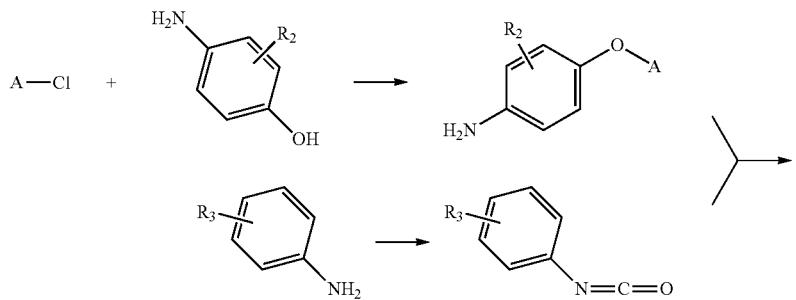

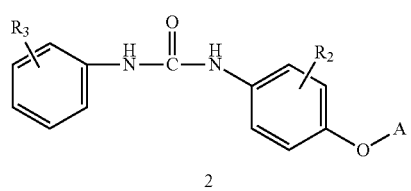 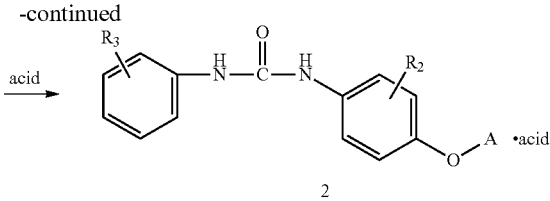

The substituents A, $R_1$, $R_2$ and $R_3$ in the above menthioned reaction routes have the above described meanings.

The beneficial effects of the present invention are as follows:

The derivatives of the present invention have raf kinase inhibitory activity. The action mechanism of this compound is that this compound affects the survival, proliferation and disease progression of tumor cells through inhibiting raf kinase and blocking the ras protein signal transduction connection, thereby inhibiting the growth of achiblastomas, such as malignant tumors (for example, bladder cancer, lung cancer, pancreatic cancer), myelopathy (for example, myelogenous leukemia) or adenoma (for example, villous adenoma of colon).

The experiment results have shown that the compound with special substituents added in A ring in the present invention has stronger antitumor activity compared with the previously disclosed compound with no substituent or only carbamyl in A ring, which is obviously stronger than Sorafenib in the effects of tumor cell metastasis and tumor angiogenesis. The test on normal human umbilical vein endothelial cells found that this part of the compounds have lower toxicity to normal human cells, such as endothelial cell, which are safe and reliable, but which can inhibit the tumor angiogenesis to achieve anti-tumor activity. In vivo nude mice transplanted model experiment proved that the compound of the present invention has inhibitory effects to human liver and kidney cancer and the effects are stronger than Sorafenib, which has more obvious effects on lung cancer and the effects are significantly better than the positive control drug Sorafenib. The results show that the compound of the present invention or pharmaceutically acceptable salts thereof can be used in the drugs for the treatment of cancer or leukemia, particularly drugs used for treating lung cancer.

DETAILED DESCRIPTION OF THE PREFERRED EMBODIMENTS

The melting point was measured by the electric melting point instrument and the thermometer was not corrected; the elemental analyzer was Foss-Heraeus type; and the mass spectrograph was electrospray ionization mass spectrometry.

A: preparing the aromatic heterocyclic substituted acardite derivate having the general formula 1 accroding to method 1

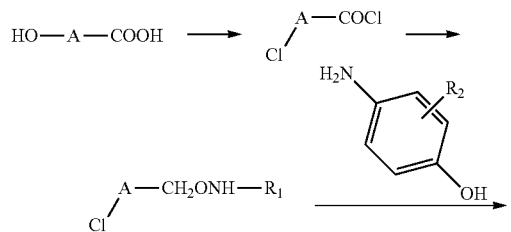

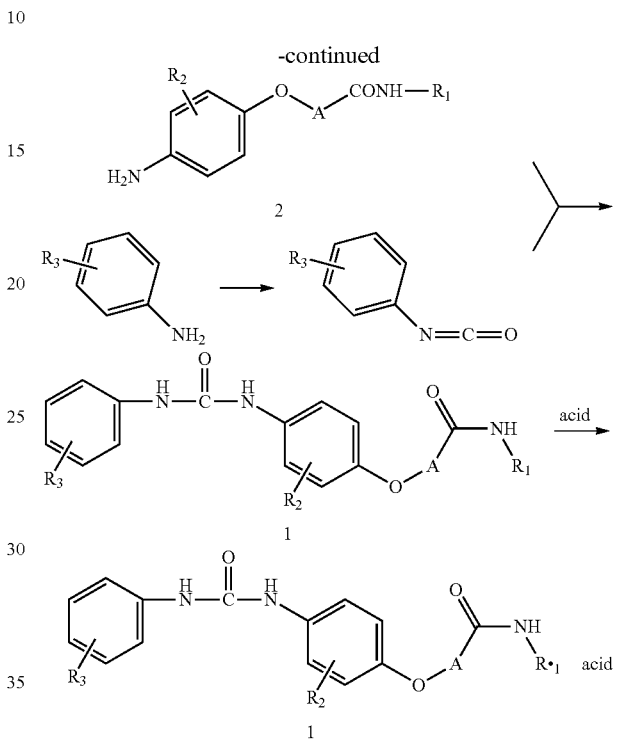

Embodiment 1: Preparation of 4-chloro-6-methoxyquinolinyl-2-carbonyl chloride 50g of 4-hydroxy-6-methoxy-2-quinolinecarboxylic acid and 100 ml of thionyl chloride were added into a three-necked flask, heated and refluxed for 17 hours until the reaction finished. The filtrate was added with toluene and concentrated under vacuum to obtain yellow solid, namely 4-chloro-6-methoxyquinolinyl-2-carbonyl chloride, with dry weight of 50g.

Embodiment 2: Preparation of 4-chloro-7-fluoroquinazolinyl-2-carbonyl chloride Prepared from 4-hydroxy-7-fluoro-2-quinazolinecarboxylic acid with reference to the method of embodiment 1.

Embodiment 3: Preparation of 4-methoxy-5-chloropyrimidine-2-carbonyl chloride Prepared from 4-methoxy-5-hydroxy-2-pyrimidinecarboxylic acid with reference to the method of embodiment 1.

Embodiment 4: Preparation of 4-chloro-7-amino-isoquinolyl-2-carbonyl chloride Prepared from 4-hydroxy-7-amino-2-quinazolinecarboxylic acid with reference to the method of embodiment 1.

Embodiment 5: Preparation of 5-methyl-4-chloropyrrolyl-2-carbonyl chloride Prepared from 5-methyl-4-hydroxy-2-pyrrolecarboxylic acid with reference to the method of embodiment 1.

Embodiment 6: Preparation of 4-chloro-6-methoxyl-N-methyl-2-quinolinyl formamide 10 g of 4-chloro-6-methoxyquinolinyl-2-carbonyl chloride (obtained from embodiment 1) was reacted with 200 ml of 2M methylamine ethanol solution under 0° C. for 36 hours until the reaction finished. The solvent was evaporated under vacuum and the residues were added with water followed by stirring evenly. Ethyl acetate was added for extracting and the ethyl acetate layer was dried with anhydrous sodium sulfate. The ethyl acetate layer was removed under vacuum to obtain 9 g of 4-chloro-6-methoxy-N-methyl-2-quinoline carboxamide.

Embodiment 7: Preparation of 4-chloro-7-fluoro-N-methyl-2-quinazoline methanamide Prepared from 4-chloro-7-fluoroquinazolinyl-2-carbonyl chloride with reference to the method of embodiment 6.

Embodiment 8: Preparation of 4-methoxyl-5-chloro-N-methyl-2-pyrimidinecarboxamide Prepared from 4-methoxyl-5-chloropyrimidinyl-2-carbonyl chloride with reference to the method of Embodiment 6.

Embodiment 9: Preparation of 4-chloro-7-amino-N-methyl-2-isoquinolinecarboxamide Prepared from 4-chloro-7-aminoisoquinolyl-2-carbonyl chloride with reference to the method of embodiment 6.

Embodiment 10: Preparation of 5-methyl-4-chloro-N-methyl-2-pyrrole carboxamide Prepared from 5-methyl-4-chloropyrryl-2-carbonyl chloride with reference to the method of embodiment 6.

Embodiment 11: Preparation of 4-(2-(N-methylaminoformoxyl)-4-(6-methoxyquinolinyl) oxy))aniline 10 g of 4-chloro-6-methoxyl-N-methyl-2-quinoline carboxamide (obtained from embodiment 6) was dissolved in DMF, added with 20 g of potassium tert-butylate and 10 g of 4-aminophenol and kept at 70° C. under the protection of nitrogen for 8 hours. After the reaction finished, the reaction solution was poured into 250 ml of ethyl acetate and 250 ml of saturated saline solution and stirred evenly for separation. The water solution was extracted with ethyl acetate again. The ethyl acetate layer was washed with saturated saline solution and dried with anhydrous sodium sulfate. The solvent was evaporated and removed under vacuum to obtain 6 g of 4-(2-(N-methylaminoformoxyl)-4-(6-methoxyquinolinyl)oxy)) aniline.

Embodiment 12: Preparation of 4-(2-(N-Methylaminoformoxyl)-4-(7Fluoroquinazolinyl) Oxy)Aniline Prepared from 4-chloro-7-fluoro-N-methyl-2-quinazoline methanamide with reference to the method of embodiment 11.

Embodiment 13: Preparation of 4-(2-(N-methylaminoformoxyl)-5-(4-methoxypyrimidinyl) oxy)aniline Prepared from 4-methoxyl-5-chloro-N-methyl-2-pyrimidinecarboxamide with reference to the method of embodiment 11.

Embodiment 14: Preparation of 4-(2-(N-Methylaminoformoxyl)-4-(7-Amino-Isoquinolyl) Oxy)Aniline Prepared from 4-chloro-7-amino-N-methyl-2-isoquinolinecarboxamide with reference to the method of embodiment 11.

Embodiment 15: Preparation of 4-(2-(N-methylaminoformoxyl)-4-(5-methyl-pyrryl)oxy) Aniline Prepared from 5-methyl-4-chloro-N-methyl-2-pyrrole carboxamide with reference to the method of embodiment 11.

Embodiment 16: Synthesis of 4-chloro-3-(trifluoromethyl)phenyl isocyanate 20 g of 4-chloro-3-(trifluoromethyl) aniline was mixed with 100 ml benzene, added with 20g of diphosgene and refluxed for 12 hours. The reaction solution was added with toluene, and the solvent was evaporated and removed under vacuum to obtain the product 4-chloro-3-(trifluoromethyl)phenyl isocyanate.

Embodiment 17: Synthesis of 4-bromo-3-(trifluoromethyl)phenyl isocyanate Prepared from 4-bromo-3-(trifluoromethyl)aniline with reference to the method of embodiment 16.

Embodiment 18: Synthesis of 4-fluoro-3-(trifluoromethyl) phenyl isocyanate Prepared from 4-fluoro-3-(trifluoromethyl)aniline with reference to the method of embodiment 16.

Embodiment 19: Synthesis of compound 17 g of 4-(2-(N-methylaminoformoxyl)-4-(6-methoxyquinolinyl)oxy)) aniline (obtained from embodiment 11), 5 g of 4-chloro-3-(trifluoromethyl)phenyl isocyanate (obtained from embodiment 16) and 50 ml of methylene dichloride were stirred at room temperature for 24 hours, and the crystals were separated out followed by air pump filtration and collection to obtain N-(4-chloro-3-(trifluoromethyl)phenyl)-N'-(4-(2-(N-methylaminoformoxyl)-4-(6-methoxyquinolinyl)oxy))phenyl)urea.

Embodiment 20: Synthesis of compound 2N-(4-fluoro-3-(trifluoromethyl)phenyl)-N'-(4-(2-(N-methylaminoformoxyl)-4-(6-methoxyquinolinyl)oxy))phenyl)urea was prepared from 4-(2-(N-methylaminoformoxyl)-4-(6-methoxyquinolinyl) oxy))anilineaniline and 4-fluoro-3-(trifluoromethyl)phenyl isocyanate according to the method of Embodiment 19.

Embodiment 21: Synthesis of compound 3N-(4-bromo-3-(trifluoromethyl)phenyl)-N'-(4-(2-(N-methylaminoformoxyl)-4-(6-methoxyquinolinyl)oxy))phenyl)urea was prepared from 4-(2-(N-methylaminoformoxyl)-4-(6-methoxyquinolinyl)oxy))aniline and 4-bromo-3-(trifluoromethyl)phenyl isocyanate according to the method of Embodiment 19.

Embodiment 22: Synthesis of compound 4N-(4-chloro-3-(trifluoromethyl)phenyl)-N'-(4-(2-(N-methylaminoformoxyl)-4-(7fluoroquinazolinyl)oxy) phenyl)urea was prepared from 4-(2-(N-methylaminoformoxyl)-4-(7fluoroquinazolinyl)oxy)aniline (obtained from embodiment 12) and 4-chloro-3-(trifluoromethyl)phenyl isocyanate according to the method of Embodiment 19.

Embodiment 23: Synthesis of compound 5N-(4-fluoro-3-(trifluoromethyl)phenyl)-N'-(4-(2-(N-methylaminoformoxyl)-4-(7fluoroquinazolinyl)oxy) phenyl)urea was prepared from 4-(2-(N-methylaminoformoxyl)-4-(7fluoroquinazolinyl)oxy)aniline and 4-fluoro-3-(trifluoromethyl)phenyl isocyanate according to the method of Embodiment 19.

Embodiment 24: Synthesis of compound 6N-(4-bromo-3-(trifluoromethyl)phenyl)-N'-(4-(2-(N-methylaminoformoxyl)-4-(7fluoroquinazolinyl)oxy) phenyl)urea was prepared from 4-(2-(N-methylaminoformoxyl)-4-(7fluoroquinazolinyl)oxy)aniline and 4-bromo-3-(trifluoromethyl)phenyl isocyanate according to the method of Embodiment 19.

Embodiment 25: Synthesis of compound 7N-(4-chloro-3-(trifluoromethyl)phenyl)-N'-(4-(2-(N-methylaminoformoxyl)-5-(4-methoxypyrimidinyl)oxy) phenyl)urea was prepared from 4-(2-(N-methylaminoformoxyl)-5-(4-methoxypyrimidinyl)oxy)aniline (obtained from embodiment 13) and 4-chloro-3-(trifluoromethyl)phenyl isocyanate according to the method of Embodiment 19.

Embodiment 26: Synthesis of compound 8N-(4-fluoro-3-(trifluoromethyl)phenyl)-N'-(4-(2-(N-methylaminoformoxyl)-5-(4-methoxypyrimidinyl)oxy) phenyl)urea was prepared from 4-(2-(N-methylaminoformoxyl)-5-(4-methoxypyrimidinyl)oxy)aniline and 4-fluoro-3-(trifluoromethyl)phenyl isocyanate according to the method of Embodiment 19.

Embodiment 27: Synthesis of compound 9N-(4-bromo-3-(trifluoromethyl)phenyl)-N'-(4-(2-(N-methylaminoformoxyl)-5-(4-methoxypyrimidinyl)oxy) phenyl)urea was prepared from 4-(2-(N-methylaminoformoxyl)-5-(4-methoxypyrimidinyl)oxy)aniline and 4-bromo-3-(trifluoromethyl)phenyl isocyanate according to the method of Embodiment 19.

Embodiment 28: Synthesis of compound 10 N-(4-chloro-3-(trifluoromethyl)phenyl)-N'-(4-(2-(N-methylaminoformoxyl)-4-(7-amino-isoquin olyl)oxy)phenyl)urea was prepared from 4-(2-(N-methylaminoformoxyl)-4-(7-amino-isoquinolyl)oxy)aniline (obtained from embodiment 14) and 4-chloro-3-(trifluoromethyl)phenyl isocyanate according to the method of Embodiment 19.

Embodiment 29: Synthesis of compound 11 N-(4-fluoro-3-(trifluoromethyl)phenyl)-N'-(4-(2-(N-methylaminoformoxyl)-4-(7-amino-isoquin olyl)oxy)phenyl)urea was prepared from 4-(2-(N-methylaminoformoxyl)-4-isoquinolyl)oxy)aniline and 4-fluoro-3-(trifluoromethyl)phenyl isocyanate according to the method of Embodiment 19.

Embodiment 30: Synthesis of compound 12 N-(4-bromo-3-(trifluoromethyl)phenyl)-N'-(4-(2-(N-methylaminoformoxyl)-4-(7-amino-isoqui nolyl)oxy)phenyl)urea was prepared from 4-(2-(N-methylaminoformoxyl)-4-isoquinolyl)oxy)aniline and 4-bromo-3-(trifluoromethyl)phenyl isocyanate according to the method of Embodiment 19.

Embodiment 31: Synthesis of compound 13 N-(4-chloro-3-(trifluoromethyl)phenyl)-N'-(4-(2-(N-methylaminoformoxyl)-4-(5-methyl-pyrryl) oxy)phenyl)urea was prepared from 4-(2-(N-methylaminoformoxyl)-4-(5-methyl-pyrryl) oxy)aniline (obtained from embodiment 15) and 4-chloro-3-(trifluoromethyl)phenyl isocyanate according to the method of Embodiment 19.

Embodiment 32: Synthesis of compound 14 N-(4-fluoro-3-(trifluoromethyl)phenyl)-N'-(4-(2-(N-methylaminoformoxyl)-4-(5-methyl-pyrryl) oxy)phenyl)urea was prepared from 4-(2-(N-methylaminoformoxyl)-4-(5-methyl-pyrryl) oxy)aniline and 4-fluoro-3-(trifluoromethyl)phenyl isocyanate according to the method of Embodiment 19.

Embodiment 33: Synthesis of compound 15 N-(4-bromo-3-(trifluoromethyl)phenyl)-N'-(4-(2-(N-methylaminoformoxyl)-4-(5-methyl-pyrryl) oxy)phenyl)urea was prepared from 4-(2-(N-methylaminoformoxyl)-4-(5-methyl-pyrryl) oxy)aniline and 4-bromo-3-(trifluoromethyl)phenyl isocyanate according to the method of Embodiment 19.

Embodiment 34: Synthesis of N-(4-chloro-3-(trifluoromethyl)phenyl)-N'-(4-(2-(N-methylaminoformoxyl)-4-(6-methoxyquino linyl)oxy))phenyl)urea mesylate 10 g of N-(4-chloro-3-(trifluoromethyl)phenyl)-N'-(4-(2-(N-methylaminoformoxyl)-4-(6-methoxyquino linyl)oxy))phenyl)urea free base was dissolved in 300 ml of ether and added with methanesulfonic acid/ethanol solution in drops at room temperature until pH=2, and white crystal was precipitated followed by air pump filtration and collection to obtain N-(4-chloro-3-(trifluoromethyl)phenyl)-N'-(4-(2-(N-methylaminoformoxyl)-4-(6-methoxyquino linyl)oxy))phenyl)urea mesylate.

Embodiment 35: Synthesis of pharmaceutically acceptable salts of N-(4-chloro-3-(trifluoromethyl)phenyl)-N'-(4-(2-(N-methylaminoformoxyl)-4-(6-methoxyquin olinyl)oxy))phenyl)urea With reference to the method of embodiment 34, fluoromethanesulfonic acid/ethanol solution, benzene sulfonic acid/ethanol solution, p-toluenesulfonic acid/ethanol solution, 1-naphthalenesulfonic acid/ethanol solution, 2-naphthalenesulfonic acid/ethanol solution, acetic acid/ethanol solution, trifluoroacetic acid/ethanol solution, malic acid/ethanol solution, tartaric acid/ethanol solution, citric acid/ethanol solution, lactic acid/ethanol solution, oxalic acid/ethanol solution, succinic acid/ethanol solution, fumaric acid/ethanol solution, maleic acid/ethanol solution, benzoic acid/ethanol solution, salicylic acid/ethanol solution, phenylacetic acid/ethanol solution or mandelic acid/ethanol solution were added in drops to synthesize trifluoromethylsulfonate, benzene sulfonate, tosilate, 1-naphthalenesulfenesulfonate, 2-naphthalenesulfenesulfonate, acetate, trifluoroactate, malate, tartrate, citrate, lactate, oxalate, succinate, fumarate, maleate, benzoate, salicylate, phenylacetate or mandelate of N-(4-chloro-3-(trifluoromethyl)phenyl)-N'-(4-(2-(N-methylaminoformoxyl)-4-(6-methoxyquino linyl)oxy))phenyl)urea.

The pharmaceutically acceptable salts of compounds 2-15 can be also synthesized according to the above mentioned method.

B: preparing the aromatic heterocyclic substituted acardite derivate having the general formula 1 accroding to method 2

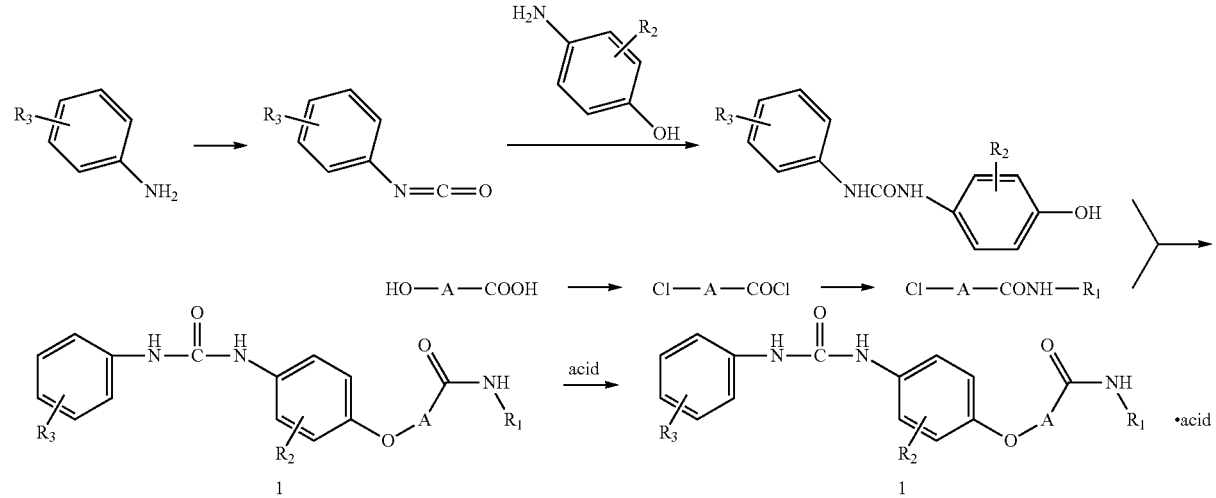

Embodiment 36: Synthesis of N-(4-chloro-3 -(trifluoromethyl)phenyl)-N'-(4-hydroxylphenyl)urea 20 g of 4-chloro-3-(trifluoromethyl)phenyl isocyanate (obtained from embodiment 16), 15 g of 4-aminophenol and 500 ml of dichloromethane were stirred at room temperature for 2 h, and the crystal was precipitated, followed by air pump filtration and collection, washing with dichloromethane and vacuum drying to obtain N-(4-chloro-3-(trifluoromethyl)phenyl)-N'-(4-hydroxylphenyl)urea.

Embodiment 37: Synthesis of N-(4-bromo-3-(trifluoromethyl)phenyl)-N'-(4-hydroxylphenyl)urea Prepared from 4-bromo-3-(trifluoromethyl)phenyl isocyanate (obtained from embodiment 17) with reference to embodiment 36.

Embodiment 38: Synthesis of N-(4-fluoro-3-(trifluoromethyl)phenyl)-N'-(4-hydroxylphenyl)urea Prepared from 4-fluoro-3-(trifluoromethyl)phenyl isocyanate (obtained from embodiment 18) with reference to embodiment 36.

Embodiment 39: Synthesis of N-(4-fluoro-3-(trifluoromethyl)phenyl)-N'-(4-(2-(N-methylaminoformoxyl)-4-(6-methoxyquino linyl)oxy))phenyl)urea (compound 1) 10 g of N-(4-chloro-3-(trifluoromethyl)phenyl)-N'-(4-hydroxylphenyl)urea (obtained from embodiment 36), 8.2 g of 4-chloro-6-methoxyl-N-methyl-2-quinoline carboxamide (obtained from embodiment 6) and 50 ml dichloromethane were stirred at room temperature for 24 h, and the crystal was precipitated, followed by air pump filtration and collection to obtain 12 g of N-(4-fluoro-3-(trifluoromethyl)phenyl)-N'-(4-(2-(N-methylaminoformoxyl)-4-(6-methoxyquino linyl)oxy))phenyl) urea.

Embodiment 40: Synthesis of compound 2N-(4-fluoro-3-(trifluoromethyl)phenyl)-N'-(4-(2-(N-methylaminoformoxyl)-4-(6-methoxyquino linyl)oxy))phenyl)urea was prepared from N-(4-fluoro-3-(trifluoromethyl)phenyl)-N'-(4-hydroxylphenyl)urea and 4-chloro-6-methoxyl-N-methyl-2-quinoline carboxamide according to the method of Embodiment 39.

Embodiment 41: Synthesis of compound 3N-(4-bromo-3-(trifluoromethyl)phenyl)-N'-(4-(2-(N-methylaminoformoxyl)-4-(6-methoxyquin olinyl)oxy))phenyl)urea was prepared from N-(4-bromo-3-(trifluoromethyl)phenyl)-N'-(4-hydroxylphenyl)urea and 4-chloro-6-methoxyl-N-methyl-2-quinoline carboxamide according to the method of Embodiment 39.

Embodiment 42: Synthesis of compound 4N-(4-chloro-3-(trifluoromethyl)phenyl)-N'-(4-(2-(N-methylaminoformoxyl)-4-(7fluoroquinazol inyl)oxy) phenyl)urea was prepared from N-(4-chloro-3-(trifluoromethyl)phenyl)-N'-(4-hydroxylphenyl)urea and 4-chloro-7-fluoro-N-methyl-2-quinazoline methanamide (obtained from embodiment 7) according to the method of Embodiment 39.

Embodiment 43: Synthesis of compound 5N-(4-fluoro-3-(trifluoromethyl)phenyl)-N'-(4-(2-(N-methylaminoformoxyl)-4-(7fluoroquinazoli nyl)oxy)phenyl)urea was prepared from N-(4-fluoro-3-(trifluoromethyl)phenyl)-N'-(4-hydroxylphenyl)urea and 4-chloro-7-fluoro-N-methyl-2-quinazoline methanamide according to the method of Embodiment 39.

Embodiment 44: Synthesis of compound 6N-(4-bromo-3-(trifluoromethyl)phenyl)-N'-(4-(2-(N-methylaminoformoxyl)-4-(7fluoroquinazol inyl)oxy)phenyl)urea was prepared from N-(4-bromo-3-(trifluoromethyl)phenyl)-N'-(4-hydroxylphenyl)urea and 4-chloro-7-fluoro-N-methyl-2-quinazoline methanamide according to the method of Embodiment 39.

Embodiment 45: Synthesis of compound 7N-(4-chloro-3-(trifluoromethyl)phenyl)-N'-(4-(2-(N-methylaminoformoxyl)-5-(4-methoxypyri midinyl)oxy) phenyl)urea was prepared from N-(4-chloro-3-(trifluoromethyl)phenyl)-N'-(4-hydroxylphenyl)urea and 4-methoxyl-5-chloro-N-methyl-2-pyrimidinecarboxamide (obtained from embodiment 8) according to the method of Embodiment 39.

Embodiment 46: Synthesis of compound 8N-(4-fluoro-3-(trifluoromethyl)phenyl)-N'-(4-(2-(N-methylaminoformoxyl)-5-(4-methoxypyrim idinyl)oxy)phenyl)urea was prepared from N-(4-fluoro-3-(trifluoromethyl)phenyl)-N'-(4-hydroxylphenyl)urea and 4-methoxyl-5-chloro-N-methyl-2-pyrimidinecarboxamide according to the method of Embodiment 39.

Embodiment 47: Synthesis of compound 9N-(4-bromo-3-(trifluoromethyl)phenyl)-N'-(4-(2-(N-methylaminoformoxyl)-5-(4-methoxypyri midinyl)oxy)phenyl)urea was prepared from N-(4-bromo-3-(trifluoromethyl)phenyl)-N'-(4-hydroxylphenyl)urea and 4-chloro-N-methyl-2-pyrimidinecarboxamide according to the method of Embodiment 39.

Embodiment 48: Synthesis of compound 10N-(4-chloro-3-(trifluoromethyl)phenyl)-N'-(4-(2-(N-methylaminoformoxyl)-4-(7-amino-isoquin olyl)oxy)phenyl)urea was prepared from N-(4-chloro-3-(trifluoromethyl)phenyl)-N'-(4-hydroxylphenyl)urea and 4-chloro-7-amino-N-methyl-2-isoquinolinecarboxamide (obtained from embodiment 9) according to the method of Embodiment 39.

Embodiment 49: Synthesis of compound 11N-(4-fluoro-3-(trifluoromethyl)phenyl)-N'-(4-(2-(N-methylaminoformoxyl)-4-(7-amino-isoquin olyl)oxy)phenyl)urea was prepared from N-(4-fluoro-3-(trifluoromethyl)phenyl)-N'-(4-hydroxylphenyl)urea and 4-chloro-7-amino-N-methyl-2-isoquinolinecarboxamide according to the method of Embodiment 39.

Embodiment 50: Synthesis of compound 12N-(4-bromo-3-(trifluoromethyl)phenyl)-N'-(4-(2-(N-methylaminoformoxyl)-4-(7-amino-isoqui nolyl)oxy)phenyl)urea was prepared from N-(4-bromo-3-(trifluoromethyl)phenyl)-N'-(4-hydroxylphenyl)urea and 4-chloro-7-amino-N-methyl-2-isoquinolinecarboxamide according to the method of Embodiment 39.

Embodiment 51: Synthesis of compound 13N-(4-chloro-3-(trifluoromethyl)phenyl)-N'-(4-(2-(N-methylaminoformoxyl)-4-(2-methyl-pyrryl) oxy)phenyl)urea was prepared from N-(4-chloro-3-(trifluoromethyl)phenyl)-N'-(4-hydroxylphenyl)urea and 2-methyl-4-chloro-N-methyl-2-pyrrole carboxamide (prepared from embodiment 10) according to the method of Embodiment 39.

Embodiment 52: Synthesis of compound 14N-(4-fluoro-3-(trifluoromethyl)phenyl)-N'-(4-(2-(N-methylaminoformoxyl)-4-(2-methyl-pyrryl) oxy)phenyl)urea was prepared from N-(4-fluoro-3-(trifluoromethyl)phenyl)-N'-(4-hydroxylphenyl)urea and 2-methyl-4-chloro-N-methyl-2-pyrrole carboxamide according to the method of Embodiment 39.

Embodiment 53: Synthesis of compound 15N-(4-bromo-3-(trifluoromethyl)phenyl)-N'-(4-(2-(N-methylaminoformoxyl)-4-(2-methyl-pyrryl) oxy)phenyl)urea was prepared from N-(4-bromo-3-(trifluoromethyl)phenyl)-N'-(4-hydroxylphenyl)urea and 2-methyl-4-chloro-N-methyl-2-pyrrole carboxamide according to the method of Embodiment 39.

C: preparing the aromatic heterocyclic substituted acardite derivate having the general formula 2 accroding to method 3

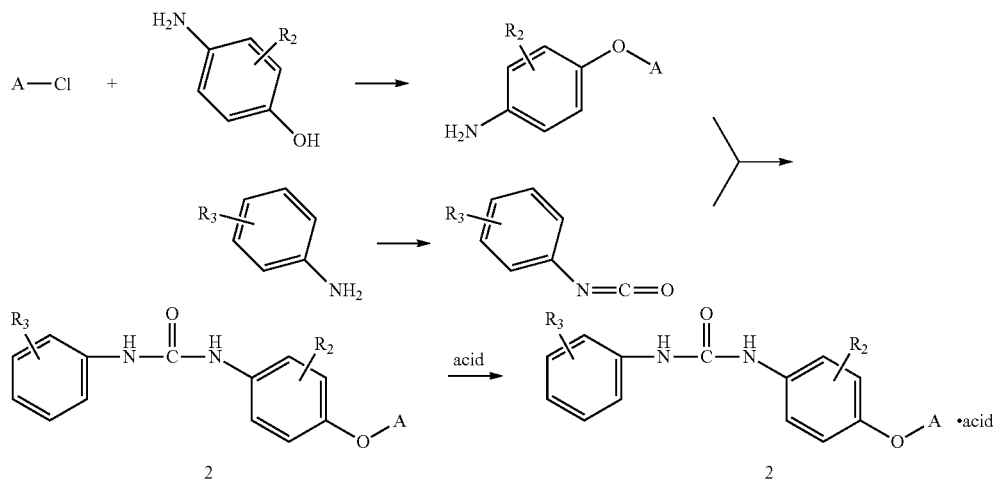

Embodiment 54: Preparation of 4-(4-(6-methoxyquinolinyl)oxy))aniline 8 g of 4-chloro-6-methoxyquinoline was dissolved in DMF, added with 20 g of potassium tert-butylate and 10 g of 4-aminophenol and reacted under the protection of nitrogen at 70° C. for 8 hours. After the end of the reaction, the reaction liquid was poured into 250 ml of ethyl acetate and 250 ml of saturated salt water and mixed evenly followed by liquid separation. The water solution was extracted with ethyl acetate.

The ethyl acetate layer was added with saturated salt water for washing and dried by anhydrous sodium sulfate. The solvent was evaporated under vacuum to obtain 6 g of 4-(4-(6-methoxyquinolinyl)oxy))aniline.

Embodiment 55: Preparation of 4-(4-(7fluoroquinazolinyl)oxy)aniline

Prepared from 4-chloroquinazoline with reference to the method of embodiment 54.

Embodiment 56: Preparation of 4-(5-(4-methoxypyrimidinyl)oxy)aniline

Prepared from 5-chloro-4-methoxypyrimidine with reference to the method of embodiment 54.

Embodiment 57: Preparation of 4-(4-(7-amino-isoquinolyl)oxy)aniline

Prepared from 4-chloro-7-aminoisoquinoline with reference to the method of embodiment 54.

Embodiment 58: Preparation of 4-(4-(2-methyl-pyrryl)oxy)aniline

Prepared from 4-chloro-2-methylpyrrol with reference to the method of embodiment 54.

Embodiment: 59: Preparation of 4-(4-(6-methoxyl-7-fluoro-quinolinyl)oxy)aniline

Prepared from 4-chloro-6-methoxyl-7-fluoro-quinoline with reference to the method of embodiment 54.

Embodiment: 60: Preparation of 4-(4-(6-methyl-7-fluoro-quinolinyl)oxy))aniline

Prepared from 4-chloro-6-methyl-7-fluoro-quinazoline with reference to the method of embodiment 54.

Embodiment 61: Synthesis of 4-chloro-3-(trifluoromethyl)phenyl isocyanate 100 ml of diphosgene is mixed with 20 g of 4-chloro-3-(trifluoromethyl)aniline and refluxed for 12 hours. The reaction liquid was added into toluene, and the solvent was evaporated under vacuum to obtain the product 4-chloro-3-(trifluoromethyl)phenyl isocyanate.

Embodiment 62: Synthesis of 4-bromo-3-(trifluoromethyl)phenyl isocyanate

Prepared from 4-bromo-3-(trifluoromethyl)aniline with reference to the method of embodiment 61.

Embodiment 63: Synthesis of 4-fluoro-3-(trifluoromethyl) phenyl isocyanate

Prepared from 4-fluoro-3-(trifluoromethyl)aniline with reference to the method of embodiment 61.

Embodiment 64: Synthesis of 4-chloro-3-ethylphenyl isocyanate

Prepared from 4-chloro-3-ethylaniline with reference to the method of embodiment 61.

Embodiment 65: Synthesis of 4-ethyl-3-trifluoromethyl

Prepared from 4-ethyl3-trifluoromethylaniline with reference to the method of embodiment 61.

Embodiment 66: Synthesis of N-(4-chloro-3-(trifluoromethyl)phenyl)-N'-(4-(4-quinolinyl)oxyphenyl)urea (compound 16) 7 g of 4-(4-(6-methoxyquinolinyl)oxy))aniline4-(4-quinolinyl)oxyaniline (prepared from embodiment 54), 5 g of 4-chloro-3-(trifluoromethyl)phenyl isocyanate (prepared from embodiment 61) and 50 ml of methylene dichloride were mixed and reacted at room temperature for 24 hours, and the crystal was precipitated, followed by air pump filtration and collection to obtain N-(4-chloro-3-(trifluoromethyl)phenyl)-N'-(4-(4-(6-methoxyquinolinyl)oxy))phenyl)urea.

Embodiment 67: Synthesis of compound 17N-(4-fluoro-3-(trifluoromethyl)phenyl)-N'-(4-(4-(6-methoxyquinolinyl)oxy))phenyl)urea was prepared from 4-(4-(6-methoxyquinolinyl)oxy))aniline and 4-fluoro-3-(trifluoromethyl)phenyl isocyanate according to the method of Embodiment 66.

Embodiment 68: Synthesis of compound 18N-(4-bromo-3-(trifluoromethyl)phenyl)-N'-(4-(4-(6-methoxyquinolinyl)oxy))phenyl)urea was prepared from 4-(4-(6-methoxyquinolinyl)oxy))aniline and 4-bromo-3-(trifluoromethyl)phenyl isocyanate according to the methd of Embodiment 66.

Embodiment 69: Synthesis of compound 19N-(4-chloro-3-(trifluoromethyl)phenyl)-N'-(4-(4-(7fluoroquinazolinyl)oxy)phenyl)urea was prepared from 4-(4-(7fluoroquinazolinyl)oxy)aniline (prepared from embodiment 55) and 4-chloro-3-(trifluoromethyl)phenyl isocyanate according to the methd of Embodiment 66.

Embodiment 70: Synthesis of compound 20N-(4-fluoro-3-(trifluoromethyl)phenyl)-N'-(4-(4-(7fluoroquinazolinyl)oxy)phenyl)urea was prepared from 4-(4-(7fluoroquinazoli- Embodiment 71: Synthesis of compound 21N-(4-bromo-3-(trifluoromethyl)phenyl)-N'-(4-(4-(7fluoroquinazolinyl)oxy)phenyl)urea was prepared from 4-(4-(7fluoroquinazolinyl)oxy)aniline and 4-bromo-3-(trifluoromethyl)phenyl isocyanate according to the methd of Embodiment 66.

Embodiment 72: Synthesis of compound 22N-(4-chloro-3-(trifluoromethyl)phenyl)-N'-(4-(5-(4-methoxypyrimidinyl)oxy)phenyl)urea was prepared from 4-(5-(4-methoxypyrimidinyl)oxy)aniline (prepared from embodiment 56) and 4-chloro-3-(trifluoromethyl)phenyl isocyanate according to the methd of Embodiment 66.

Embodiment 73: Synthesis of compound 23N-(4-fluoro-3-(trifluoromethyl)phenyl)-N'-(4-(5-(4-methoxypyrimidinyl)oxy)phenyl)urea was prepared from 4-(5-(4-methoxypyrimidinyl)oxy)aniline and 4-fluoro-3-(trifluoromethyl)phenyl isocyanate according to the methd of Embodiment 66.

Embodiment 74: Synthesis of compound 24N-(4-bromo-3-(trifluoromethyl)phenyl)-N'-(4-(5-(4-methoxypyrimidinyl)oxy)phenyl)urea was prepared from 4-(5-(4-methoxypyrimidinyl)oxy)aniline and 4-bromo-3-(trifluoromethyl)phenyl isocyanate according to the methd of Embodiment 66.

Embodiment 75: Synthesis of compound 25N-(4-chloro-3-(trifluoromethyl)phenyl)-N'-(4-(4-(7-amino-isoquinolyl)oxy)phenyl)urea was prepared from 4-(4-(7-amino-isoquinolyl)oxy)aniline (prepared from embodiment 57) and 4-chloro-3-(trifluoromethyl)phenyl isocyanate according to the methd of Embodiment 66.

Embodiment 76: Synthesis of compound 26N-(4-fluoro-3-(trifluoromethyl)phenyl)-N'-(4-(4-(7-amino-isoquinolyl)oxy)phenyl)urea was prepared from 4-(4-(7-amino-isoquinolyl)oxy)aniline and 4-fluoro-3-(trifluoromethyl)phenyl isocyanate according to the methd of Embodiment 66.

Embodiment 77: Synthesis of compound 27N-(4-bromo-3-(trifluoromethyl)phenyl)-N'-(4-(4-(7-amino-isoquinolyl)oxy)phenyl)urea was prepared from 4-(4-(7-amino-isoquinolyl)oxy)aniline and 4-bromo-3-(trifluoromethyl)phenyl isocyanate according to the methd of Embodiment 66.

Embodiment 78: Synthesis of compound 28N-(4-chloro-3-(trifluoromethyl)phenyl)-N'-(4-(4-(2-methyl-pyrryl)oxy)phenyl)urea was prepared from 4-(4-(2-methyl-pyrryl)oxy)aniline (prepared from embodiment 58) and 4-chloro-3-(trifluoromethyl)phenyl isocyanate according to the methd of Embodiment 66.

Embodiment 79: Synthesis of compound 29N-(4-fluoro-3-(trifluoromethyl)phenyl)-N'-(4-(4-(2-methyl-pyrryl)oxy)phenyl)urea was prepared from 4-(4-(5-methyl-pyrryl)oxy)aniline and 4-fluoro-3-(trifluoromethyl)phenyl isocyanate according to the methd of Embodiment 66.

Embodiment 80: Synthesis of compound 30N-(4-bromo-3-(trifluoromethyl)phenyl)-N'-(4-(4-(2-methyl-pyrryl)oxy)phenyl)urea was prepared from 4-(4-(5-methyl-pyrryl)oxy)aniline and 4-bromo-3-(trifluoromethyl)phenyl isocyanate according to the methd of Embodiment 66.

Embodiment 81: Synthesis of compound 31N-(4-chloro-3-ethylphenyl)-N'-(4-(4-(6-methoxyl-7-fluoro-quinolinyl)oxy)phenyl)urea was prepared from 4-(4-(6-methoxyl-7-fluoro-quinolinyl)oxy)aniline (prepared from embodiment 59) and 4-chloro-3-ethylphenyl isocyanate (prepared from embodiment 64) according to the methd of Embodiment 66.

Embodiment 82: Synthesis of compound 32N-(4-ethyl-3-(trifluoromethyl)phenyl)-N'-(4-(4-(6-methoxyl-7-fluoro-quinolinyl)oxy)phenyl)urea was prepared from 4-(4-(6-methoxyl-7-fluoro-quinolinyl)oxy)aniline (prepared from embodiment 59) and 4-ethyl-3-trifluoromethyl isocyanate (prepared from embodiment 65) according to the methd of Embodiment 66.

Embodiment 83: Synthesis of compound 33N-(4-chloro-3-ethylphenyl)-N'-(4-(4-(6-methyl-7-fluoro-quinolinyl)oxy))phenyl)urea was prepared from 4-(4-(6-methyl-7-fluoro-quinolinyl)oxy))aniline (prepared from embodiment 60) and 4-chloro-3-ethylphenyl isocyanate (prepared from embodiment 64) according to the methd of Embodiment 66.

Embodiment 84: Synthesis of compound 34N-(4-ethyl-3-(trifluoromethyl)phenyl)-N'-(4-(4-(6-methyl-7-fluoro-quinolinyl)oxy))phenyl)urea was prepared from 4-(4-(6-methyl-7-fluoro-quinolinyl)oxy))aniline (prepared from embodiment 60) and 4-ethyl-3-trifluoromethyl isocyanate (prepared from embodiment 65) according to the methd of Embodiment 66.

Embodiment 85: Preparation of 4-chloro-7-nitrylquinoline-2-carbonyl chloride Prepared from 4-hydroxyl-7-nitryl-2-quinoline carboxylic acid with reference to the method of embodiment 1.

Embodiment 86: Preparation of 4-chloro-7-trifluoromethylquinazoline-2-carbonyl chloride Prepared from 4-hydroxyl-7-trifluoromethyl-2-quinazoline carboxylic acid with reference to the method of embodiment 1.

Embodiment 87: Preparation of 4-chloro-7-nitryl-N-ethyl-2-quinoline carboxamide Prepared from 4-chloro-7-nitrylquinoline-2-carbonyl chloride (prepared from embodiment 58) and 2M ethylamine ethanol solution with reference to the method of embodiment 6.

Embodiment 88: Preparation of 4-chloro-7-trifluoromethyl-N-propyl-2-quinazoline methanamide Prepared from 4-chloro-7-trifluoromethylquinazoline-2-carbonyl chloride (prepared from embodiment 86) and 2M propylamine ethanol solution with reference to the method of embodiment 6.

Embodiment 89: Preparation of 2-methyl-4-(2-(N-ethylcarbamyl)-4-(7-nitrylquinolinyl)oxy))aniline Prepared from 4-chloro-7-nitryl-N-ethyl-2-quinoline carboxamide (prepared from embodiment 87) and 3-methyl-4-aminophenol with reference to the method of embodiment 11.

Embodiment 90: Preparation of 2-methoxyl-4-(2-(N-ethylcarbamyl)-4-(7-nitrylquinolinyl)oxy))aniline Prepared from 4-chloro-7-nitryl-N-ethyl-2-quinoline carboxamide (prepared from embodiment 87) and 3-methoxyl-4-aminophenol with reference to the method of embodiment 11.

Embodiment 91: Preparation of 2-fluoro-4-(2-(N-propylcarbamyl)-4-(7-trifluoromethylquinolinyl)oxy)) aniline Prepared from 4-chloro-7-trifluoromethyl-N-propyl-2-quinazoline methanamide (prepared from embodiment 88) and 3-fluoro-4-aminophenol with reference to the method of embodiment 11.

Embodiment 92: Preparation of 2-trifluoromethyl-4-(2-(N-propylcarbamyl)-4-(7-trifluoromethylquinolinyl)oxy)) aniline Prepared from 4-chloro-7-trifluoromethyl-N-propyl-2-quinazoline methanamide (prepared from embodiment 88) and 4-amino-3-trifluoromethyl phenol with reference to the method of embodiment 11.

Embodiment 93: Synthesis of 4-chloro-3-methoxyphenyl isocyanate Prepared from 4-chloro-3-methoxyaniline with reference to the method of embodiment 61.

Embodiment 94: Preparation of compound 35N-(4-chloro-3-methoxyphenyl)-N'-(2-methyl-4-(2-(N-ethylcarbamyl)-4-(7-nitryl-quinolinyl)ox y)phenyl)urea was sythesized from 2-methyl-4-(2-(N-ethylcarbamyl)-4-(7-nitrylquinolinyl)oxy))aniline (prepared from embodiment 89) and 4-chloro-3-methoxyphenyl isocyanate (prepared from embodiment 93) according to the method of Embodiment 19.

Embodiment 95: Preparation of compound 36 N-(4-chloro-3-methoxyphenyl)-N'-(2-methoxyl-4-(2-(N-ethylcarbamyl)-4-(7-nitryl-quinolinyl) oxy)phenyl)urea was sythesized from 2-methoxyl-4-(2-(N-ethylcarbamyl)-4-(7-nitrylquinolinyl)oxy))aniline (prepared from embodiment 90) and 4-chloro-3-methoxyphenyl isocyanate (prepared from embodiment 93) according to the method of Embodiment 19.

Embodiment 96: Preparation of compound 37 N-(4-chloro-3-methoxyphenyl)-N'-(2-fluoro-4-(2-(N-propylcarbamyl)-4-(7-trifluoromethylqui nolinyl)oxy))phenyl)urea was sythesized from 2-fluoro-4-(2-(N-propylcarbamyl)-4-(7-trifluoromethylquinolinyl)oxy))aniline (prepared from embodiment 91) and 4-chloro-3-methoxyphenyl isocyanate (prepared from embodiment 93) according to the method of Embodiment 19.

Embodiment 97: Preparation of compound 38 N-(4-chloro-3-methoxyphenyl)-N'-(2-trifluoromethyl-4-(2-(N-propylcarbamyl)-4-(7-trifluorom ethylquinolinyl)oxy))phenyl)urea was sythesized from 2-trifluoromethyl-4-(2-(N-propylcarbamyl)-4-(7-trifluoromethylquinolinyl)oxy))aniline (prepared from embodiment 92) and 4-chloro-3-methoxyphenyl isocyanate (prepared from embodiment 93) according to the method of Embodiment 19.

Embodiment 98: Synthesis of N-(4-chloro-3-(trifluoromethyl)phenyl)-N'-(4-(4-(6-methoxyquinolinyl)oxy))phenyl)urea mesylate 10 g of N-(4-chloro-3-(trifluoromethyl)phenyl)-N'-(4-(4-(6-methoxyquinolinyl)oxy))phenyl)urea free base was dissolved in 300 ml of ether and added with methanesulfonic acid/ethanol solution in drops at room temperature until pH=2, and white crystal was precipitated followed by air pump filtration and collection to obtain N-(4-chloro-3-(trifluoromethyl)phenyl)-N'-(4-(4-(6-methoxyquinolinyl)oxy))phenyl)urea mesylate.

Embodiment 99: Synthesis of pharmaceutically acceptable salts of N-(4-chloro-3-(trifluoromethyl)phenyl)-N'-(4-(4-(6-methoxyquinolinyl)oxy))phenyl)urea With reference to the method of embodiment 85, fluoromethanesulfonic acid/ethanol solution, benzene sulfonic acid/ethanol solution, p-toluenesulfonic acid/ethanol solution, 1-naphthalenesulfonic acid/ethanol solution, 2-naphthalenesulfonic acid/ethanol solution, acetic acid/ethanol solution, trifluoroacetic acid/ethanol solution, malic acid/ethanol solution, tartaric acid/ethanol solution, citric acid/ethanol solution, lactic acid/ethanol solution, oxalic acid/ethanol solution, succinic acid/ethanol solution, fumaric acid/ethanol solution, maleic acid/ethanol solution, benzoic acid/ethanol solution, salicylic acid/ethanol solution, phenylacetic acid/ethanol solution or mandelic acid/ethanol solution were added in drops to synthesize trifluoromethylsulfonate, benzene sulfonate, tosilate, 1-naphthalenesulfenesulfonate, 2-naphthalenesulfenesulfonate, acetate, trifluoroactate, malate, tartrate, citrate, lactate, oxalate, succinate, fumarate, maleate, benzoate, salicylate, phenylacetate or mandelate of N-(4-chloro-3-(trifluoromethyl)phenyl)-N'-(4-(4-quinolinyl)oxyphenyl)urea.

The pharmaceutically acceptable salts of compounds 17-38 can be also synthesized according to the above mentioned method.

The compounds in table 1 to 14 were prepared according to methods of the above mentioned embodiments, and the characteristics are shown in the following tables.

TABLE 1 substituted quinoline derivatives

A = quinolyl (the substituent is 6-methoxy)
$R_1$ = methyl, $R_2$ = H

| Compound No. | $R_3$ | Elementary analysis | Name | Mass spectrum M + 1 |
|---|---|---|---|---|
| 1 | 4-chloro-3-trifluoromethyl | C: 57.3 H: 3.8 N: 10.3 | N-(4-chloro-3-(trifluoromethyl)phenyl)-N'-(4-(2-(N-methylaminoformoxyl)-4-(6-methoxyquinolinyl)oxy))phenyl)urea | 545.5 |
| 2 | 4-fluoro-3-trifluoromethyl | C: 59.2 H: 3.9 N: 10.5 | N-(4-fluoro-3-(trifluoromethyl)phenyl)-N'-(4-(2-(N-methylaminoformoxyl)-4-(6-methoxyquinolinyl)oxy))phenyl)urea | 529 |
| 3 | 4-bromo-3-trifluoromethyl | C: 53.0 H: 3.31 N: 9.38 | N-(4-bromo-3-(trifluoromethyl)phenyl)-N'-(4-(2-(N-methylaminoformoxyl)-4-(6-methoxyquinolinyl)oxy))phenyl)urea | 590 |

TABLE 2 substituted quinazoline derivatives

A = quinazolinyl (the substituent is 7-fluoro)
$R_1$ = methyl, $R_2$ = H

| Compound No. | $R_3$ | Elementary analysis | Name | Mass spectrum M + 1 |
|---|---|---|---|---|
| 4 | 4-chloro-3-trifluoromethyl | C: 54.1 H: 3.11 N: 13.0 | N-(4-chloro-3-(trifluoromethyl)phenyl)-N'-(4-(2-(N-methylaminoformoxyl)-4-(7 fluoroquinazolinyl)oxy)phenyl)urea | 534.5 |
| 5 | 4-fluoro-3-trifluoromethyl | C: 55.5 H: 3.30 N: 13.4 | N-(4-fluoro-3-(trifluoromethyl)phenyl)-N'-(4-(2-(N-methylaminoformoxyl)-4-(7 fluoroquinazolinyl)oxy)phenyl)urea | 518 |
| 6 | 4-bromo-3-trifluoromethyl | C: 49.7 H: 2.91 N: 12.2 | N-(4-bromo-3-(trifluoromethyl)phenyl)-N'-(4-(2-(N-methylaminoformoxyl)-4-(7 fluoroquinazolinyl)oxy)phenyl)urea | 579 |

TABLE 3 substituted pyrimidine derivatives

A = pyrimidine (the substituent is 4-methoxy)
$R_1$ = methyl, $R_2$ = H

| Compound No. | $R_3$ | Elementary analysis | Name | Mass spectrum m/e |
|---|---|---|---|---|
| 7 | 4-chloro-3-trifluoromethyl | C: 50.9 H: 3.48 N: 14.0 | N-(4-chloro-3-(trifluoromethyl)phenyl)-N'-(4-(2-(N-methylaminoformoxyl)-5-(4-methoxypyrimidinyl)oxy)phenyl)urea | 496.5 |
| 8 | 4-fluoro-3-trifluoromethyl | C: 52.5 H: 3.67 N: 14.5 | N-(4-fluoro-3-(trifluoromethyl)phenyl)-N'-(4-(2-(N-methylaminoformoxyl)-5-(4-methoxypyrimidinyl)oxy)phenyl)urea | 480 |
| 9 | 4-bromo-3-trifluoromethyl | C: 46.8 H: 3.00 N: 13.1 | N-(4-bromo-3-(trifluoromethyl)phenyl)-N'-(4-(2-(N-methylaminoformoxyl)-5-(4-methoxypyrimidinyl)oxy)phenyl)urea | 541 |

TABLE 4 substituted isoquinoline derivatives

A = isoquinoline (the substituent is 7-amino)
$R_1$ = methyl, $R_2$ = H

| Compound No. | $R_3$ | Elementary analysis | Name | Mass spectrum m/e |
|---|---|---|---|---|
| 10 | 4-chloro-3-trifluoromethyl | C: 56.5  H: 3.70  N: 13.2 | N-(4-chloro-3-(trifluoromethyl)phenyl)-N'-(4-(2-(N-methylaminoformoxyl)-4-(7-amino-isoquinolyl)oxy)phenyl)urea | 530.5 |
| 11 | 4-fluoro-3-trifluoromethyl | C: 58.5  H: 3.81  N: 13.8 | N-(4-fluoro-3-(trifluoromethyl)phenyl)-N'-(4-(2-(N-methylaminoformoxyl)-4-(7-amino-isoquinolyl)oxy)phenyl)urea | 514 |
| 12 | 4-bromo-3-trifluoromethyl | C: 52.4  H: 3.44  N: 12.4 | N-(4-bromo-3-(trifluoromethyl)phenyl)-N'-(4-(2-(N-methylaminoformoxyl)-4-(7-amino-isoquinolyl)oxy)phenyl)urea | 574 |

TABLE 5 substituted pyrrole derivatives

A = pyrrole (the substituent is 5-methyl)
$R_1$ = methyl, $R_2$ = H

| Compound No. | $R_3$ | Elementary analysis | Name | Mass spectrum m/e |
|---|---|---|---|---|
| 13 | 4-chloro-3-trifluoromethyl | C: 54.1  H: 4.01  N: 12.2 | N-(4-chloro-3-(trifluoromethyl)phenyl)-N'-(4-(2-(N-methylaminoformoxyl)-4-(5-methyl-pyrryl)oxy)phenyl)urea | 467.5 |
| 14 | 4-fluoro-3-trifluoromethyl | C: 55.8  H: 4.02  N: 12.6 | N-(4-fluoro-3-(trifluoromethyl)phenyl)-N'-(4-(2-(N-methylaminoformoxyl)-4-(5-methyl-pyrryl)oxy)phenyl)urea | 451 |
| 15 | 4-bromo-3-trifluoromethyl | C: 49.5  H: 3.70  N: 11.0 | N-(4-bromo-3-(trifluoromethyl)phenyl)-N'-(4-(2-(N-methylaminoformoxyl)-4-(5-methyl-pyrryl)oxy)phenyl)urea | 511 |

TABLE 6 substituted quinoline derivatives

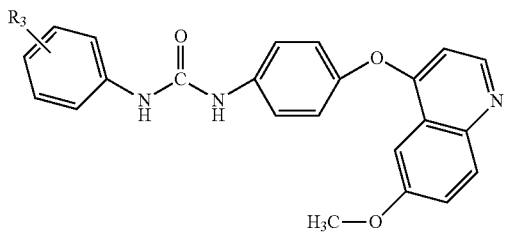

A = quinoline (the substituent is 6-methoxy),
$R_2$ = H

| Compound No. | $R_3$ | Elementary analysis | Name | Mass spectrum m/e |
|---|---|---|---|---|
| 16 | 4-chloro-3-trifluoromethyl | C: 59.2 H: 3.70 N: 8.77 | N-(4-chloro-3-(trifluoromethyl)phenyl)-N'-(4-(4-(6-methoxyquinolinyl)oxy))phenyl)urea | 488.5 |
| 17 | 4-fluoro-3-trifluoromethyl | C: 61.3 H: 3.81 N: 8.80 | N-(4-fluoro-3-(trifluoromethyl)phenyl)-N'-(4-(4-(6-methoxyquinolinyl)oxy))phenyl)urea | 472 |
| 18 | 4-bromo-3-trifluoromethyl | C: 54.0 H: 3.40 N: 7.79 | N-(4-bromo-3-(trifluoromethyl)phenyl)-N'-(4-(4-(6-methoxyquinolinyl)oxy))phenyl)urea | 532 |

TABLE 7 substituted quinazoline derivatives

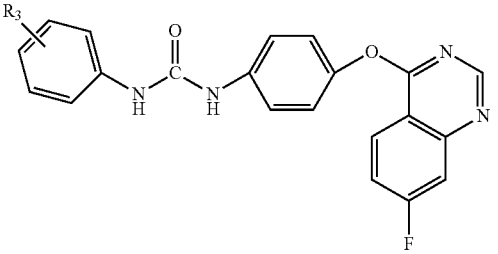

A = quinazoline (the substituent is 7-fluoro),
$R_2$ = H

| Compound No. | $R_3$ | Elementary analysis | Name | Mass spectrum m/e |
|---|---|---|---|---|
| 19 | 4-chloro-3-trifluoromethyl | C: 55.5 H: 2.91 N: 11.6 | N-(4-chloro-3-(trifluoromethyl)phenyl)-N'-(4-(4-(7 fluoroquinazolinyl)oxy)phenyl)urea | 477.5 |
| 20 | 4-fluoro-3-trifluoromethyl | C: 57.7 H: 2.75 N: 12.2 | N-(4-fluoro-3-(trifluoromethyl)phenyl)-N'-(4-(4-(7 fluoroquinazolinyl)oxy)phenyl)urea | 461 |
| 21 | 4-bromo-3-trifluoromethyl | C: 50.5 H: 2.71 N: 10.8 | N-(4-bromo-3-(trifluoromethyl)phenyl)-N'-(4-(4-(7 fluoroquinazolinyl)oxy)phenyl)urea | 522 |

TABLE 8 substituted pyrimidine derivatives

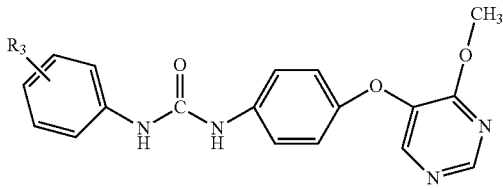

A = pyrimidine (the substituent is 4-methoxy),
R₂ = H

| Compound No. | R₃ | Elementary analysis | Name | Mass spectrum m/e |
|---|---|---|---|---|
| 22 | 4-chloro-3-trifluoromethyl | C: 52.1 H: 3.30 N: 12.8 | N-(4-chloro-3-(trifluoromethyl)phenyl)-N'-(4-(5-(4-methoxypyrimidinyl)oxy)phenyl) | 439.5 |
| 23 | 4-fluoro-3-trifluoromethyl | C: 54.2 H: 3.38 N: 13.3 | N-(4-fluoro-3-(trifluoromethyl)phenyl)-N'-(4-(5-(4-methoxypyrimidinyl)oxy)phenyl) | 423 |
| 24 | 4-bromo-3-trifluoromethyl | C: 47.2 H: 2.99 N: 11.4 | N-(4-bromo-3-(trifluoromethyl)phenyl)-N'-(4-(5-(4-methoxypyrimidinyl)oxy)phenyl) | 484 |

TABLE 9 substituted isoquinoline derivatives

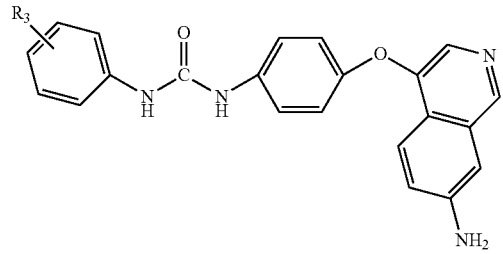

A = isoquinoline (the substituent is 7-amino),
R₂ = H

| Compound No. | R₃ | Elementary analysis % | Name | Mass spectrum m/e |
|---|---|---|---|---|
| 25 | 4-chloro-3-trifluoromethyl | C: 58.4 H: 3.38 N: 11.81 | N-(4-chloro-3-(trifluoromethyl)phenyl)-N'-(4-(4-(7-amino-isoquinolyl)oxy)phenyl)urea | 473.5 |
| 26 | 4-fluoro-3-trifluoromethyl | C: 60.7 H: 3.70 N: 13.5 | N-(4-fluoro-3-(trifluoromethyl)phenyl)-N'-(4-(4-(7-amino-isoquinolyl)oxy)phenyl)urea | 457 |
| 27 | 4-bromo-3-trifluoromethyl | C: 53.5 H: 3.40 N: 10.7 | N-(4-bromo-3-(trifluoromethyl)phenyl)-N'-(4-(4-(7-amino-isoquinolyl)oxy)phenyl)urea | 518 |

TABLE 10 substituted pyrrole derivatives

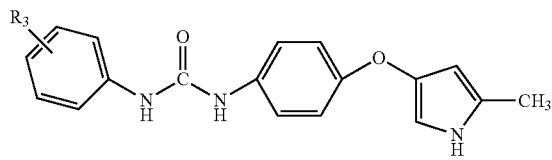

A = pyrrole (the substituent is 2-methyl),
$R_2 = H$

| Compound No. | $R_3$ | Elementary analysis % | Name | Mass spectrum m/e |
|---|---|---|---|---|
| 28 | 4-chloro-3-trifluoromethyl | C: 55.7 H: 3.75 N: 10.4 | N-(4-chloro-3-(trifluoromethyl)phenyl)-N'-(4-(4-(2-methyl-pyrryl)oxy)phenyl)urea | 410.5 |
| 29 | 4-fluoro-3-trifluoromethyl | C: 58.2 H: 4.01 N %: 10.5 | N-(4-fluoro-3-(trifluoromethyl)phenyl)-N'-(4-(4-(2-methyl-pyrryl)oxy)phenyl)urea | 395 |
| 30 | 4-bromo-3-trifluoromethyl | C: 50.3 H: 3.49 N: 9.41 | N-(4-bromo-3-(trifluoromethyl)phenyl)-N'-(4-(4-(2-methyl-pyrryl)oxy)phenyl)urea | 455 |

TABLE 11 polysubstituted quinoline derivatives

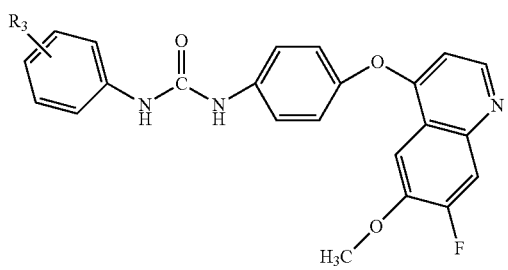

A = quinoline (the substituent is 6-methoxyl-7-fluoro),
$R_2 = H$

| Compound No. | $R_3$ | Elementary analysis | Name | Mass spectrum m/e |
|---|---|---|---|---|
| 31 | 4-chloro-3-ethyl | C: 64.6 H: 4.71 N: 9.20 | N-(4-chloro-3-ethylphenyl)-N'-(4-(4-(6-methoxyl-7-fluoro-quinolinyl)oxy)phenyl)urea | 466.5 |
| 32 | 4-ethyl-3-trifluoromethyl | C: 62.7 H: 4.36 N: 8.22 | N-(4-ethyl-3-(trifluoromethyl)phenyl)-N'-(4-(4-(6-methoxyl-7-fluoro-quinolinyl)oxy)phenyl)urea | 501.5 |

TABLE 12 polysubstituted quinazoline derivatives

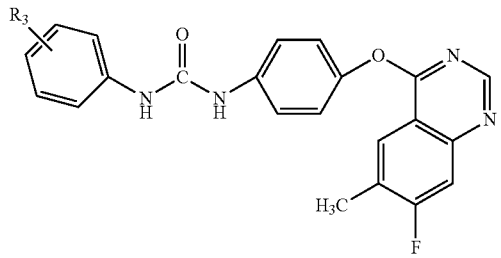

A = quinazoline (the substituent is 6-methyl-7-fluoro),
$R_2$ = H

| Compound No. | $R_3$ | Elementary analysis | Name | Mass spectrum m/e |
|---|---|---|---|---|
| 33 | 4-chloro-3-ethyl | C: 64.1 H: 4.70 N: 12.3 | N-(4-chloro-3-ethylphenyl)-N'-(4-(4-(6-methyl-7-fluoro-quinolinyl)oxy)phenyl)urea | 451.5 |
| 34 | 4-ethyl-3-trifluoromethyl | C: 61.8 H: 4.01 N: 11.38 | N-(4-ethyl-3-(trifluoromethyl)phenyl)-N'-(4-(4-(6-methyl-7-fluoro-quinolinyl)oxy)phenyl)urea | 485 |

TABLE 13 substituted quinoline derivatives

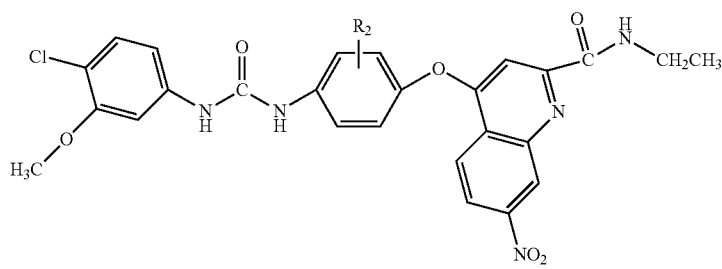

A = quinoline (the substituent is 7-nitryl),
$R_1$ = ethyl, $R_3$ = 4-chloro-3-methoxy

| Compound No. | $R_2$ | Elementary analysis | Name | Mass spectrum m/e |
|---|---|---|---|---|
| 35 | 2-methyl | C: 59.1 H: 4.32 N: 12.5 | N-(4-chloro-3-methoxyphenyl)-N'-(2-methyl-4-(2-(N-ethylcarbamyl)-4-(7-nitryl-quinolinyl)oxy)phenyl)urea | 550.5 |
| 36 | 2-methoxy | C: 57.2 H: 4.36 N: 12.2 | N-(4-chloro-3-methoxyphenyl)-N'-(2-methoxyl-4-(2-(N-ethylcarbamyl)-4-(7-nitryl-quinolinyl)oxy)phenyl)urea | 566.5 |

TABLE 14 substituted quinazoline derivatives

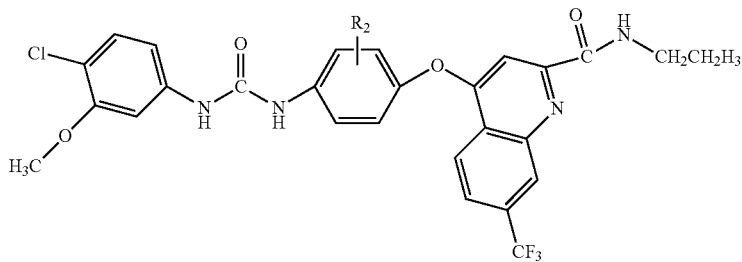

A = quinazoline (the substituent is 7-trifluoromethyl),
$R_1$ = propyl, $R_3$ = 4-chloro-3-methoxy

| Compound No. | $R_2$ | Elementary analysis | Name | Mass spectrum m/e |
|---|---|---|---|---|
| 37 | 2-fluoro | C: 56.1<br>H: 4.17<br>N: 9.72 | N-(4-chloro-3-methoxyphenyl)-N'-(2-fluoro-4-(2-(N-propylcarbamyl)-4-(7-trifluoromethylquinolinyl)oxy))phenyl)urea | 579.5 |
| 38 | 2-trifluoro-methyl | C: 53.4<br>H: 3.91<br>N: 8.58 | N-(4-chloro-3-methoxyphenyl)-N'-(2-trifluoromethyl-4-(2-(N-propylcarbamyl)-4-(7-trifluoromethylquinolinyl)oxy))phenyl)urea | 629.5 |

Determination of Antitumor Activity

1. Inhibitory activity of the compound of the present invention on raf kinase

[Test Method]
Raf-1 inhibitor screening by chemoluminescence method
[Instruments]
Westernblot electrophoresis apparatus Rotaryshaker
[Test Materials]
Raf-1(truncated), Magnesium/ATP Cocktail, MEK1 unactive

[Tested Samples]
Compounds 1-38
[Positive Control]
Sorafenib $$\text{Inhibiton rate \%} = \frac{\text{Gray value of the negative control group} - \text{gray value of the drug-treated group}}{\text{Gray value of the negative control group}} \times 100\%$$

[Results]

TABLE 13

Inhibition of compounds 1-16 and positive control medicine on raf kinase

| Compound No. | Final concentration $1.0*10^{-5}$ mol/ml | Inhibition rate % | Activity | Compound No. | Final concentration $1.0*10^{-5}$ mol/ml | Inhibition rate % | Activity |
|---|---|---|---|---|---|---|---|
| 1 | 1 | 75.0 | + | 9 | 1 | 99.2 | + |
| 2 | 1 | 61.1 | + | 10 | 1 | 3.5 | |
| 3 | 1 | 56.3 | + | 11 | 1 | 11.2 | |
| 4 | 1 | 82.2 | + | 12 | 1 | 12.1 | |
| 5 | 1 | 98.9 | + | 13 | 1 | 55.0 | + |
| 6 | 1 | 80.1 | + | 14 | 1 | 41.3 | |
| 7 | 1 | 99.1 | + | 15 | 1 | 35.5 | |
| 8 | 1 | 44..5 | | 16 | 1 | 62.1 | + |
| Positive control medicine | 1 | 85.7 | + | | | | |

TABLE 14

Inhibition of compounds 17-38 and positive control medicine on raf kinase

| Compound No. | Final concentration $1.0*10^{-5}$ mol/ml | Inhibition rate % | Activity | Compound No. | Final concentration $1.0*10^{-5}$ mol/ml | Inhibition rate % | Activity |
|---|---|---|---|---|---|---|---|
| 17 | 1 | 58.2 | + | 28 | 1 | 33.5 | |
| 18 | 1 | 34.4 | | 29 | 1 | 85.3 | + |
| 19 | 1 | 93.5 | + | 30 | 1 | 16.8 | |
| 20 | 1 | 87.7 | + | 31 | 1 | 89.4 | + |
| 21 | 1 | 98.9 | + | 32 | 1 | 90.5 | + |
| 22 | 1 | 88.1 | + | 33 | 1 | 92.3 | + |

TABLE 14-continued

Inhibition of compounds 17-38 and positive control medicine on raf kinase

| Compound No. | Final concentration $1.0*10^{-5}$ mol/ml | Inhibition rate % | Activity | Compound No. | Final concentration $1.0*10^{-5}$ mol/ml | Inhibition rate % | Activity |
|---|---|---|---|---|---|---|---|
| 23 | 1 | 89.9 | + | 34 | 1 | 96.2 | + |
| 24 | 1 | 91.3 | + | 35 | 1 | 45.3 | |
| 25 | 1 | 11.5 | | 36 | 1 | 81.2 | + |
| 26 | 1 | 15.3 | | 37 | 1 | 81.5 | + |
| 27 | 1 | 8.8 | | 38 | 1 | 88.1 | + |
| Positive control medicine | 1 | 85.7 | + | | | | |

The test results of inhibitory activity of the compound on raf kinase showed that the inhibitory activity of the compound in the present invention is better than or equivalent to positive control medicine sorafenib. The test results indicate that these compounds can affect the survival, proliferation and disease progression of tumor cells through inhibiting the raf kinase and blocking the ras protein signal transduction cascade of tumor cells. The compound of the present invention has potential of being applied to treat tumor and leukemia.

2. Experimental therapeutic action of the compound in the present invention on S180 sarcoma mice

[Test Materials]

Test animals: ICR mice, 18-25 g

Tumor types: mice S180 sarcoma, provided by Shanghai Institute of Materia Medica, Chinese Academy of Sciences.

Positive control medicine: Sorafenib

Tested samples: compounds 1-38

[Test Method]

18-25 g female ICR mice and well grown 7-11 day old mice sarcoma S180 tumor seeds were selected, and the seeds were inoculated into the subcutaneous at the right axillary. After inoculated 24 hours, these mice were randomly divided into cages and orally administrated 60 mg/kg for 9 days. On 10 day, the animals were killed and weighed, and the tumor weights were weighed to calculate average tumor weight in each group, followed by calculating the tumor inhibition rate according to the following formula and T test.

$$\text{Tumor growth inhibition rate} = \frac{\text{Average tumor weight in the control group} - \text{average tumor weight in the treatment group}}{\text{average tumor weight in the treatment group}} \times 100\%$$

[Determination Results]

TABLE 15

Tumor growth inhibition rate of compounds 1-3 and sorafenib on mice S180 sarcoma

| Groups | Dosage | Administration methods | Animal number Start | Animal number Final | Weight (g) Start | Weight (g) Final | Tumor weight x ± SD(g) | Inhibition rate (%) | P value |
|---|---|---|---|---|---|---|---|---|---|
| Normal saline | 0.4 ml/mouse | ig | 20 | 20 | 18.9 ± 1.5 | 22.0 ± 3.4 | 1.61 ± 0.36 | | |
| Sora | 60 mg/kg | ig | 10 | 10 | 18.8 ± 1.2 | 21.7 ± 2.4 | 0.71 ± 0.30 | 55.9 | <0.05 |
| Compound 1 | 60 mg/kg | ig | 10 | 10 | 18.7 ± 1.9 | 22.3 ± 1.3 | 0.99 ± 0.20 | 38.5 | <0.05 |
| Compound 2 | 60 mg/kg | ig | 10 | 10 | 18.9 ± 1.7 | 20.9 ± 2.3 | 0.87 ± 0.24 | 46.0 | <0.05 |
| Compound 3 | 60 mg/kg | ig | 10 | 10 | 18.0 ± 1.1 | 20.2 ± 2.5 | 0.75 ± 0.36 | 53.4 | <0.05 |

TABLE 16

Tumor growth inhibition rate of compounds 1-12 and sorafenib on mice S180 sarcoma (%)

| | 1 | 2 | 3 | 4 | 5 | 6 | 7 | 8 | 9 | 10 | 11 | 12 | Sorafenib |
|---|---|---|---|---|---|---|---|---|---|---|---|---|---|
| Mice S180 sarcoma | 38.5 | 24.1 | 53.4 | 50.1 | 49.3 | 51.2 | 21.5 | 58.2 | 55.9 | 55.2 | 54.2 | 45.7 | 55.9% |

TABLE 17

Tumor growth inhibition rate of compounds 13-26 and sorafenib on mice S180 sarcoma (%)

| | 13 | 14 | 15 | 16 | 17 | 18 | 19 | 20 | 21 | 22 | 23 | 24 | 25 | 26 |
|---|---|---|---|---|---|---|---|---|---|---|---|---|---|---|
| Mice S180 sarcoma | 21.2 | 18.2 | 56.7 | 33.6 | 44.2 | 35.7 | 50.8 | 54.6 | 59.7 | 52.1 | 51.5 | 54.6 | 55.8 | 7.6 |

TABLE 18

Tumor growth inhibition rate of compounds 27-38 and sorafenib on mice S180 sarcoma (%)

| | 27 | 28 | 29 | 30 | 31 | 32 | 33 | 34 | 35 | 36 | 37 | 38 |
|---|---|---|---|---|---|---|---|---|---|---|---|---|
| Mice S180 sarcoma | 55.1 | 11.5 | 14.2 | 55.2 | 50.3 | 49.8 | 55.3 | 52.6 | 55.8 | 55.1 | 24.1 | 59.2 |

3. Experimental therapeutic action of the compound in the present invention on Human colon cancer HT-29 transplantable tumor in nude mice.

[Test Materials]

Test animals: Female BALB/cA nude mice, 35-40 day old, with weight of 18-22 g.

Tumor seeds: Human colon cancer HT-29 transplantable tumor in nude mice, established by inoculating human colon cancer HT-29 cell strains subcutaneously in nude mice Positive control medicine: Sorafenib Tested samples: Compounds 1-38

[Test Method]

Take eugenic tumor tissues and cut into about 1.5 mm³, and then inoculate subcutaneously at the right armpit of nude mice under the sterile conditions. The diameter of the transplantable tumor in nude mice was determined with a vernier caliper, and the animals were divided into groups after the tumors were grown to 100-300 mm³. Using the method of measuring the tumor diameter, dynamically observe the anti-tumor effects of tested materials. The diameter of the tumor was determined three times every week and the mouse weight was weighed at the same time. The mice were intragastrically administrated with Sorafenib and tested drugs, 60 mg/kg, for continuous 9 times. The solvent was intragastrically administrated as the control for continuous 9 times. Equal amount of control was administrated in the negative control group.

Tumor volume (TV) is calculated as: $TV = \frac{1}{2} \times a \times b^2$, wherein a and b respectively represent length and width.

Relative tumor volume (RTV) is calculated as: $RTV = TV_t / TV_0$, wherein $TV_0$ is the tumor volume when administrated according to different cages and $TV_t$ is the tumor volume measured each time.

Relative tumor reproduction rate T/C (%) is calculated as follows:

$$T/C(\%) = \frac{T_{RTV}}{C_{RTV}} \times 100$$

$T_{RTV}$: RTV in the treatment group; $C_{RTV}$: RTV in the negative control group.

The test results used relative tumor reproduction rate T/C (%) as evaluating indicator of anti-tumor activity.

Evaluation of in vivo anti-tumor activity

| T/C % | Evaluation |
|---|---|
| ≥60 | (−) No activity |
| 60-50 | (+/−) Marginal activity |
| 50-40 | (+) Moderate-strength activity |
| 40-10 | (++) High-strength activity |
| ≤10 | (+++) Extremely high-strength activity |

[Determination results]

TABLE 19

Experimental treatment of compounds 1-3 and Sorafenib on human colon cancer HT-29 transplantable tumor in nude mice

| Groups | Dosage mg/kg | Animal number Start | Animal number Final | Weight (g) d0 | Weight (g) d13 | TV d0 | TV d13 | RTV | T/C (%) |
|---|---|---|---|---|---|---|---|---|---|
| Control | | 6 | 6 | 18.8 ± 1.1 | 19.6 ± 0.9 | 133 ± 60 | 626 ± 226 | 5.07 ± 1.39 | |
| Solvent control | | 6 | 6 | 19.7 ± 0.6 | 20.8 ± 0.8 | 133 ± 32 | 547 ± 172 | 4.15 ± 0.93 | 81.85 |
| Sorafenib | 60 | 6 | 6 | 19.9 ± 1.1 | 20.4 ± 1.4 | 133 ± 33 | 308 ± 86 | 2.36 ± 0.57 | 46.48** |
| Compound 1 | 60 | 6 | 6 | 19.5 ± 1.0 | 20.5 ± 1.1 | 128 ± 34 | 359 ± 108 | 2.81 ± 1.05 | 55.42** |
| Compound 2 | 60 | 6 | 6 | 19.9 ± 0.8 | 21.0 ± 0.8 | 133 ± 23 | 265 ± 100 | 2.00 ± 0.41 | 39.45** |
| Compound 3 | 60 | 6 | 6 | 19.1 ± 1.0 | 19.7 ± 1.4 | 133 ± 18 | 322 ± 129 | 2.40 ± 0.67 | 47.34** |

TABLE 20

Relative tumor reproduction rate of compounds 1-10 and Sorafenib on Human colon cancer HT-29 transplantable tumor in nude mice T/C (%)

| | 1 | 2 | 3 | 4 | 5 | 6 | 7 | 8 | 9 | 10 | Sorafenib |
|---|---|---|---|---|---|---|---|---|---|---|---|
| Human colon cancer HT-29 transplantable tumor in nude mice | 55.42 | 39.45 | 47.34 | 33.15 | 38.24 | 39.58 | 40.1 | 37.6 | 35.2 | 78.9 | 46.48 |

TABLE 21

Relative tumor reproduction rate of compounds 11-20 and Sorafenib on human colon cancer HT-29 transplantable tumor in nude mice T/C (%)

| | 11 | 12 | 13 | 14 | 15 | 16 | 17 | 18 | 19 | 20 |
|---|---|---|---|---|---|---|---|---|---|---|
| Human colon cancer HT-29 transplantable tumor in nude mice | 81.2 | 80.5 | 81.2 | 40.1 | 85.2 | 55.2 | 54.7 | 40.2 | 39.4 | 40.1 |

TABLE 22

Relative tumor reproduction rate of compounds 21-30 and Sorafenib on human colon cancer HT-29 transplantable tumor in nude mice T/C (%)

| | 21 | 22 | 23 | 24 | 25 | 26 | 27 | 28 | 29 | 30 |
|---|---|---|---|---|---|---|---|---|---|---|
| Human colon cancer HT-29 transplatable tumor in nude mice | 38.7 | 41.2 | 39.7 | 37.8 | 79.5 | 41.1 | 80.3 | 39.1 | 78.3 | 79.5 |

TABLE 23

Relative tumor reproduction rate of compounds 31-38 and Sorafenib on human colon cancer HT-29 transplantable tumor in nude mice T/C (%)

| | 31 | 32 | 33 | 34 | 35 | 36 | 37 | 38 |
|---|---|---|---|---|---|---|---|---|
| Human colon cancer HT-29 transplantable tumor in nude mice | 50.3 | 46.2 | 39.9 | 45.9 | 51.2 | 41.5 | 39.5 | 41.2 |

The results of the above in vivo and vitro tumor inhibition tests showed that the inhibiting effects of such derivatives on S180 sarcoma in mice and human colon cancer HT-29 transplantable tumor in nude mice were better than or equivalent to positive control medicine sorafenib. The test results showed that the compound of the present invention or the pharmaceutically acceptable salt thereof can be used for treating tumor or leukemia. The pharmacodynamic experiments of the compounds in the present invention, positive control medicine sorafenib and compounds A', B' and C' with no substituent or only amino formyl in A ring on human lung cancer cell strain A549, human high-metastic lung cancer cell strain 95D, lung cancer cell A549, human umbilical vein endothelial cell HUVEC cell growth and lumen formation, human lung cancer A549 cell transplantation tumor model in nude mice, human liver cancer cell bel-7402 transplantation tumor model in nude mice, and renal carcinoma cell line GCR-1 transplantation tumor model in nude mice were carried out to verify the effect of the compounds of the present invention.

Sorafenib was abbreviated as Sorafenib hereafter, and the compounds A', B' and C' were respectively prepared according the method of CN200810129360.6, which were compounds with no substituent in A ring, wherein A' is N-(4-chloro-3-(trifluoromethyl)phenyl)-N'-(4-(4-quinolinyl)oxy)phenyl)urea, B' is N-(4-chloro-3-(trifluoromethyl)phenyl)-N'-(4-(4-pyrimidinyl)oxy)phenyl)urea, and C' is N-(4-fluoro-3-(trifluoromethyl)phenyl)-N'-(4-(4-pyrryl)oxy)phenyl)urea.

4. Using 3-(4,5-dimethylthiazol-2-yl)-2,5-diphenyl tetrazolium bromide assay (MTT) to detect the inhibition effects on the growth of human lung cancer cell strain A549

[Test materials] MTT working solution, F12 medium containing 10% FBS, continuous injectors

[Tested compound] Compounds 1-38

[Positive control medicine] Sorafenib, compounds A', B', C' with no substituent or only amino formyl in A ring The inhibition rate is calculated as follows:

Cell reproduction rate % =

$$1 - \frac{\left(\begin{array}{c}\text{Relative } OD \text{ value of } control \text{ well} - \\ \text{Relative } OD \text{ value of drug well}\end{array}\right)}{\text{Relative } OD \text{ value of } control \text{ well}} \times 100\%$$

Relative OD value of conrol well=OD value of control well–OD value of blank well Relative OD value of drug well=OD value of drug well–OD value of blank well

[Screening Results]

TABLE 24

Inhibition effects of compounds 1-18 on the growth of human lung cancer cell A549

| Compound No. | Final concentration $1.0*10^{(-5)}$ mol/L | Inhibition rate | Activity |
|---|---|---|---|
| 1 | 1 | 50.20% | + |
| 2 | 1 | 61.11% | ++ |
| 3 | 1 | 69.67% | ++ |
| 4 | 1 | 91.12% | +++ |
| 5 | 1 | 93.50% | +++ |
| 6 | 1 | 92.50% | +++ |
| 7 | 1 | 45.30% | + |
| 8 | 1 | 60.67% | ++ |
| 9 | 1 | 61.54% | ++ |
| 10 | 1 | 74.50% | ++ |
| 11 | 1 | 69.20% | ++ |
| 12 | 1 | 42.31% | + |
| 13 | 1 | 64.23% | ++ |

TABLE 24-continued

Inhibition effects of compounds 1-18 on the growth of human lung cancer cell A549

| Compound No. | Final concentration $1.0*10^{(-5)}$ mol/L | Inhibition rate | Activity |
|---|---|---|---|
| 14 | 1 | 67.25% | ++ |
| 15 | 1 | 72.17% | ++ |
| 16 | 1 | 89.71% | +++ |
| 17 | 1 | 88.52% | +++ |
| 18 | 1 | 90.71% | +++ |

TABLE 25

Inhibition effects of compounds 19-38 on the growth of human lung cancer cell A549

| Compound No. | Final concentration $1.0*10^{(-5)}$ mol/ml | Inhibition rate | Activity |
|---|---|---|---|
| 19 | 1 | 91.23% | +++ |
| 20 | 1 | 88.32% | +++ |
| 21 | 1 | 89.21% | +++ |
| 22 | 1 | 82.49% | +++ |
| 23 | 1 | 55.41% | + |
| 24 | 1 | 86.32% | +++ |
| 25 | 1 | 63.26% | + |
| 26 | 1 | 55.50% | + |
| 27 | 1 | 64.71% | + |
| 28 | 1 | 88.52% | +++ |
| 29 | 1 | 86.42% | +++ |
| 30 | 1 | 85.47% | +++ |
| 31 | 1 | 46.78% | + |
| 32 | 1 | 45.76% | + |
| 33 | 1 | 57.53% | + |
| 34 | 1 | 59.52% | + |
| 35 | 1 | 55.74% | + |
| 36 | 1 | 72.45% | ++ |
| 37 | 1 | 71.65% | ++ |
| 38 | 1 | 74.56% | ++ |
| Posive Sorafenib | 1 | 54.60% | + |
| Compound A' | 1 | 58.51% | + |
| Compound B' | 1 | 61.62% | + |
| Compound C' | 1 | 62.25% | + |

5 Inhibition effects of compounds on human high-metastic lung cancer cell 95D migration

[Test materials] Boyden Chamber Transwell chamber (with pore size of 8 μm), human high-metastic lung cancer cell 95D cell strain, 1640 medium containing 10% FBS, 1640 medium containing no serum

[Tested compound] Compounds 1-38

[Positive control medicine] Sorafenib, compounds A', B', C' with no substituent or only amino formyl in A ring The inhibition rate is calculated as follows:

$$\text{Cell migration inhibition rate \%} = \frac{\left(\begin{array}{c}\text{migrated cell number in the chamber containing no drug}-\\ \text{migrated cell number in the chamber containing drug}\end{array}\right)}{\text{migrated cell number in the chamber containing no drug}} \times 100\%$$

[Screening Results]

TABLE 26

Inhibition effects of compounds 1-18 on human high-metastic lung cancer 95D cell strain migration

| Compound No. | Final concentration $1.0*10^{(-5)}$ mol/L | Inhibition rate | Activity |
|---|---|---|---|
| 1 | 1 | 80.21% | ++ |
| 2 | 1 | 85.17% | +++ |
| 3 | 1 | 96.64% | +++ |
| 4 | 1 | 96.38% | +++ |
| 5 | 1 | 97.51% | +++ |
| 6 | 1 | 93.71% | +++ |
| 7 | 1 | 89.34% | +++ |
| 8 | 1 | 89.56% | +++ |
| 9 | 1 | 91.42% | +++ |
| 10 | 1 | 61.43% | + |
| 11 | 1 | 78.66% | ++ |
| 12 | 1 | 66.79% | ++ |
| 13 | 1 | 65.45% | ++ |
| 14 | 1 | 57.57% | + |
| 15 | 1 | 63.68% | + |
| 16 | 1 | 89.31% | +++ |
| 17 | 1 | 90.52% | +++ |
| 18 | 1 | 93.73% | +++ |

TABLE 27

Inhibition effects of compounds 19-38 on human high-metastic lung cancer 95D cell strain migration

| Compound No. | Final concentration $1.0*10^{(-5)}$ mol/L | Inhibition rate | Activity |
|---|---|---|---|
| 19 | 1 | 90.21% | +++ |
| 20 | 1 | 89.12% | +++ |
| 21 | 1 | 88.76% | +++ |
| 22 | 1 | 88.77% | +++ |
| 23 | 1 | 85.53% | +++ |
| 24 | 1 | 85.48% | +++ |
| 25 | 1 | 59.76% | + |
| 26 | 1 | 60.52% | + |
| 27 | 1 | 59.77% | + |
| 28 | 1 | 70.53% | + |
| 29 | 1 | 61.44% | + |
| 30 | 1 | 69.62% | ++ |
| 31 | 1 | 76.18% | ++ |
| 32 | 1 | 66.92% | ++ |
| 33 | 1 | 77.52% | ++ |
| 34 | 1 | 63.65% | + |
| 35 | 1 | 68.47% | ++ |
| 36 | 1 | 84.59% | +++ |
| 37 | 1 | 79.25% | + |
| 38 | 1 | 80.53% | + |
| Positive Sorafenib | 1 | 62.32% | + |
| Compound A' | 1 | 63.51% | + |
| Compound B' | 1 | 61.60% | + |
| Compound C' | 1 | 63.20% | ++ |

6. Effects of tested compounds on the adhesive ability of lung cancer cell A549

[Test materials] gelatin, CCK8, poly-lysine (PLL), A549 cell stains, 1640 medium containing 10% FBS

[Tested compound] Compounds 1-38 to be tested

[Positive control medicine] Sorafenib, compounds A', B', C' with no substituent or only amino formyl in A ring

[Screening Results]
The inhibition rate is calculated as follows:

Inhibition rate of cell adhesion % =

$$\frac{\begin{array}{c}\text{Cell group without treatment}\\\text{(glutin adhesion }OD/PLL\text{ adhesion }OD\text{ value)} -\\\text{dosing cell group(glutin adhesion }OD/PLL\text{ adhesion }OD\text{ value)}\end{array}}{\begin{array}{c}\text{Cell group without treatment}\\\text{(glutin adhesion }OD/PLL\text{ adhesion }OD\text{ value)}\end{array}} \times$$

100%

Dosing dosing cells without cell group (gelatin adhesive OD/PLL adhesion OD)–Dosing cell group (gelatin adhesive OD/PLL adhesion OD value)
Dosing dosing cells without cell group (gelatin adhesive OD/PLL adhesion OD value)

TABLE 28

Inhibition effects of compounds 1-18 on the adhesion ability of human lung cancer cell A549

| Compound No. | Final concentration $1.0*10^{(-5)}$ mol/L | Inhibition rate | Activity |
|---|---|---|---|
| 1 | 1 | 60.22% | + |
| 2 | 1 | 75.15% | ++ |
| 3 | 1 | 79.66% | ++ |
| 4 | 1 | 89.71% | +++ |
| 5 | 1 | 87.58% | +++ |
| 6 | 1 | 93.59% | +++ |
| 7 | 1 | 68.34% | ++ |
| 8 | 1 | 61.56% | + |
| 9 | 1 | 85.32% | +++ |
| 10 | 1 | 64.57% | + |
| 11 | 1 | 59.63% | + |
| 12 | 1 | 62.30% | + |
| 13 | 1 | 63.39% | + |
| 14 | 1 | 67.51% | ++ |
| 15 | 1 | 68.63% | ++ |
| 16 | 1 | 90.77% | +++ |
| 17 | 1 | 97.50% | +++ |
| 18 | 1 | 93.72% | +++ |

TABLE 29

Inhibition effects of compounds 19-38 on the adhesion ability of human lung cancer cell A549

| Compound No. | Final concentration $1.0*10^{(-5)}$ mol/L | Inhibition rate | Activity |
|---|---|---|---|
| 19 | 1 | 90.28% | +++ |
| 20 | 1 | 95.31% | +++ |
| 21 | 1 | 90.22% | +++ |
| 22 | 1 | 72.44% | ++ |
| 23 | 1 | 77.56% | ++ |
| 24 | 1 | 73.30% | ++ |
| 25 | 1 | 63.51% | + |
| 26 | 1 | 68.57% | ++ |
| 27 | 1 | 94.77% | +++ |
| 28 | 1 | 90.53% | +++ |
| 29 | 1 | 91.40% | +++ |
| 30 | 1 | 92.44% | +++ |
| 31 | 1 | 66.77% | ++ |
| 32 | 1 | 64.73% | + |
| 33 | 1 | 77.59% | ++ |
| 34 | 1 | 76.54% | ++ |
| 35 | 1 | 75.72% | ++ |
| 36 | 1 | 74.50% | ++ |
| 37 | 1 | 71.74% | ++ |
| 38 | 1 | 75.53% | ++ |
| Positive medicine Sorafenib | 1 | 72.66% | ++ |
| Compound A' | 1 | 71.55% | ++ |
| Compound B' | 1 | 69.26% | ++ |
| Compound C' | 1 | 68.62% | ++ |

7. Effects of tested compounds on the growth of human umbilical vein endothelial cell HUVEC cell by CCK8 method

[Test materials] CCK8, human umbilical vein endothelial cell HUVEC cell, 1640 medium containing 10% FBS
[Tested compound] Compounds 1-38 to be tested
[Positive control medicine] Sorafenib, compounds A', B', C' with no substituent or only amino formyl in A ring
[Screening Results]

Cell reproduction rate % =

$$1 - \frac{\left(\begin{array}{c}\text{Relative }OD\text{ value of }conrol\text{ well} -\\ \text{Relative }OD\text{ value of drug well}\end{array}\right)}{\text{Relative }OD\text{ value of }conrol\text{ well}} \times 100\%$$

Relative OD value of conrol well=OD value of control well–OD value of blank well
Relative OD value of drug well=OD value of drug well–OD value of blank well

TABLE 30

Inhibition effects of compounds 1-18 on the growth of human umbilical vein endothelial cell HUVEC cell

| Compound No. | Final concentration $1.0*10^{(-5)}$ mol/L | Inhibition rate | Activity |
|---|---|---|---|
| 1 | 1 | 9.20% | |
| 2 | 1 | 13.11% | |
| 3 | 1 | 27.67% | |
| 4 | 1 | 5.12% | |
| 5 | 1 | 8.50% | |
| 6 | 1 | 7.50% | |
| 7 | 1 | 8.30% | |
| 8 | 1 | 13.67% | |
| 9 | 1 | 11.54% | |
| 10 | 1 | 14.50% | |
| 11 | 1 | 29.20% | |
| 12 | 1 | 12.31% | |
| 13 | 1 | 24.23% | |
| 14 | 1 | 17.25% | |
| 15 | 1 | 38.17% | |
| 16 | 1 | 10.71% | |
| 17 | 1 | 13.52% | |
| 18 | 1 | 5.71% | |

TABLE 31

Inhibition effects of compounds 19-38 on the growth of human umbilical vein endothelial cell HUVEC cell

| Compound No. | Final concentration $1.0*10^{(-5)}$ mol/L | Inhibition rate | Activity |
|---|---|---|---|
| 19 | 1 | 5.23% | |
| 20 | 1 | 7.32% | |
| 21 | 1 | 11.21% | |

TABLE 31-continued

Inhibition effects of compounds 19-38 on the growth of human umbilical vein endothelial cell HUVEC cell

| Compound No. | Final concentration 1.0*10^(-5) mol/L | Inhibition rate | Activity |
|---|---|---|---|
| 22 | 1 | 12.49% | |
| 23 | 1 | 17.41% | |
| 24 | 1 | 13.32% | |
| 25 | 1 | 23.26% | |
| 26 | 1 | 32.50% | |
| 27 | 1 | 24.73% | |
| 28 | 1 | 20.55% | |
| 29 | 1 | 21.40% | |
| 30 | 1 | 25.46% | |
| 31 | 1 | 26.70% | |
| 32 | 1 | 24.77% | |
| 33 | 1 | 17.50% | |
| 34 | 1 | 19.52% | |
| 35 | 1 | 5.74% | |
| 36 | 1 | 12.45% | |
| 37 | 1 | 19.65% | |
| 38 | 1 | 14.56% | |
| Positive medicine Sorafenib | 1 | 22.61% | |
| Compound A' | 1 | 23.11% | |
| Compound B' | 1 | 31.64% | |
| Compound C' | 1 | 22.27% | |

8. Inhibition effects of compounds on the lumen formation ability of human umbilical vein endothelial cell HUVEC

[Experimental principles] The human umbilical vein endothelial cells have ability of spontaneously forming blood lumen on Matrigel, which can be used to simulate the process of angiogenesis in vivo. We used Matrigel method to investigate the effects of the compound on the lumen formation ability of human umbilical vein endothelial cell HUVEC.

[Test materials] HUVEC (taking generation 3 to 5 cells for experiments after obtained from primary separation and cultured at 37 under the conditions of 5% $CO_2$), Matrigel, cell culture medium M199.

[Tested compound] Compounds 1-38
[Positive control medicine] Sorafenib, compounds A', B', C' with no substituent or only amino formyl in A ring
[Screening Results]
The inhibition rate is calculated as follows:

Lumen formation inhibition rate % =

$$\frac{\text{length sum of lumen without dosing} - \text{length sum of lumen after dosing}}{\text{length sum of lumen without dosing}} \times 100\%$$

TABLE 32

Inhibition effects of compounds 1-18 on the lumen formation ability of human umbilical vein endothelial cell HUVEC

| Compound No. | Final concentration 1.0*10^(-5) mol/L | Inhibition rate | Activity |
|---|---|---|---|
| 1 | 1 | 72.22% | ++ |
| 2 | 1 | 75.14% | ++ |
| 3 | 1 | 76.61% | ++ |
| 4 | 1 | 86.77% | +++ |
| 5 | 1 | 87.50% | +++ |
| 6 | 1 | 90.55% | +++ |
| 7 | 1 | 60.34% | + |
| 8 | 1 | 78.59% | ++ |
| 9 | 1 | 91.45% | +++ |
| 10 | 1 | 50.34% | + |
| 11 | 1 | 79.63% | ++ |
| 12 | 1 | 52.37% | + |
| 13 | 1 | 53.36% | + |
| 14 | 1 | 67.53% | ++ |
| 15 | 1 | 68.64% | ++ |
| 16 | 1 | 80.79% | ++ |
| 17 | 1 | 67.50% | ++ |
| 18 | 1 | 63.71% | + |

TABLE 33

Inhibition effects of compounds 19-38 on the lumen formation ability of human umbilical vein endothelial cell HUVEC

| Compound No. | Final concentration 1.0*10^(-5) mol/L | Inhibition rate | Activity |
|---|---|---|---|
| 19 | 1 | 89.22% | +++ |
| 20 | 1 | 88.54% | +++ |
| 21 | 1 | 89.47% | +++ |
| 22 | 1 | 86.72% | +++ |
| 23 | 1 | 97.56% | +++ |
| 24 | 1 | 93.78% | +++ |
| 25 | 1 | 79.79% | ++ |
| 26 | 1 | 70.53% | ++ |
| 27 | 1 | 89.75% | +++ |
| 28 | 1 | 89.52% | +++ |
| 29 | 1 | 86.43% | +++ |
| 30 | 1 | 90.66% | +++ |
| 31 | 1 | 66.77% | ++ |
| 32 | 1 | 54.74% | + |
| 33 | 1 | 67.51% | ++ |
| 34 | 1 | 66.52% | ++ |
| 35 | 1 | 65.70% | ++ |
| 36 | 1 | 64.50% | + |
| 37 | 1 | 71.72% | ++ |
| 38 | 1 | 65.55% | ++ |
| Positive medicine Sorafenib | 1 | 55.60% | ++ |
| Compound A' | 1 | 60.51% | ++ |
| Compound B' | 1 | 61.62% | ++ |
| Compound C' | 1 | 60.50% | ++ |

9. Tumor inhibition rate of tested compounds on human lung cancer A549 cell transplantation model in nude mice

[Test animals] female BALB/cA nude mice, 35-40 days old, with weight of 18-22g. There were 12 mice in the negative conrol group and 6 mice in the treatment group.

[Test method] Take eugenic tumor tissues and cut into about 1.5 $mm^3$, and then inoculate subcutaneously at the right armpit of nude mice under the sterile conditions. The diameter of the transplantable tumor in nude mice was determined with a vernier caliper, and the animals were divided into groups after the tumors were grown to 100-300 $mm^3$. Using the method of measuring the tumor diameter, dynamically observe the antitumor effects of tested materials.

The diameter of the tumor was determined three times every week and the mouse weight was weighed at the same time. The dosage of the compound was 60 mg/kg, 6 times every week for 3 weeks. Sorafenib was oral administrated with dosage of 60 mg/kg, 6 times every week for 3 weeks. Equal amount of normal saline was administrated in the negative control group. Observe for one week after administration.

[Detection Indicators and Calculation Methods]
(1) Tumor volume (TV) is calculated as:

$TV = \frac{1}{2} \times a \times b^2$ wherein a and b respectively represents length and width.

(2) Relative tumor volume (RTV) is calculated as:

$RTV = TV_t/TV_0$ wherein $TV_0$ is the tumor volume when administrated according to different cages and $TV_t$ is the tumor volume measured each time.

(3) Relative tumor reproduction rate T/C (%) is calculated as follows:

$$T/C(\%) = \frac{T_{RTV}}{C_{RTV}} \times 100$$

$T_{RTV}$: RTV in the treatment group; $C_{RTV}$: RTV in the negative control group. The test results used relative tumor reproduction rate T/C (%) as evaluating indicator of anti-tumor activity.

[Screening results] There was no mortality for the animals in the group of compounds and Sorafenib in the experiments with less toxicity.

TABLE 34

Relative tumor reproduction rate of compounds and Sorafenib on human lung cancer A549 transplantation tumor in nude mice T/C (%)

Relative tumor reproduction rate of compounds 1-10 and Sorafenib on human lung cancer A549 transplantation tumor in nude mice T/C (%)

| | 1 | 2 | 3 | 4 | 5 | 6 | 7 | 8 | 9 | 10 |
|---|---|---|---|---|---|---|---|---|---|---|
| human lung cancer A549 transplantation tumor | 38.7 | 35.3 | 37.2 | 12.3 | 11.6 | 15.9 | 39.3 | 30.5 | 38.7 | 30.1 |

Relative tumor reproduction rate of compounds 11-20 and Sorafenib on human lung cancer A549 transplantation tumor in nude mice T/C (%)

| | 11 | 12 | 13 | 14 | 15 | 16 | 17 | 18 | 19 | 20 |
|---|---|---|---|---|---|---|---|---|---|---|
| human lung cancer A549 transplantation tumor | 43.7 | 36.3 | 38.4 | 32.2 | 38.7 | 9.9 | 7.3 | 12.5 | 7.7 | 12.1 |

Relative tumor reproduction rate of compounds 21-30 and Sorafenib on human lung cancer A549 transplantation tumor in nude mice T/C (%)

| | 21 | 22 | 23 | 24 | 25 | 26 | 27 | 28 | 29 | 30 |
|---|---|---|---|---|---|---|---|---|---|---|
| human lung cancer A549 transplantation tumor | 13.7 | 15.3 | 17.1 | 15.6 | 39.4 | 33.1 | 36.3 | 13.6 | 14.7 | 13.1 |

Relative tumor reproduction rate of compounds 31-38 and Sorafenib on human lung cancer A549 transplantation tumor in nude mice T/C (%)

| | 31 | 32 | 33 | 34 | 35 | 36 | 37 | 38 | Sorafenib |
|---|---|---|---|---|---|---|---|---|---|
| human lung cancer A549 transplantation tumor | 38.7 | 35.3 | 37.5 | 22.3 | 23.6 | 37.9 | 38.3 | 36.5 | 41.8 |

| | Compound A' | Compound B' | Compound C' |
|---|---|---|---|
| human lung cancer A549 transplantation tumor | 43.2 | 40.4 | 36.6 |

10. Tumor inhibition rate of tested compounds on human liver cancer cell bel-7402 transplantation tumor model in nude mice

[Test animals] female BALB/cA nude mice, 35-40 days old, with weight of 18-22g. There were 12 mice in the negative control group and 6 mice in the treatment group.

[Test method] Take eugenic tumor tissues and cut into about 1.5 mm³, and then incoculate subcutaneously at the right armpit of nude mice under the sterile conditions. The diameter of the transplantable tumor in nude mice was determined with a vernier caliper, and the animals were divided into groups after the tumors were grown to 100-300 mm³. Using the method of measuring the tumor diameter, dynamically observe the antitumor effects of tested materials.

The diameter of the tumor was determined three times every week and the mouse weight was weighed at the same time. The dosage of the compound was 60 mg/kg, 6 times every week for 3 weeks. Sorafenib was oral administrated with dosage of 60 mg/kg, 6 times every week for 3 weeks. Equal amount of normal saline was administrated in the negative control group. Observe for one week after administration.

[Detection Indicators and Calculation Methods]
(1) Tumor volume (TV) is calculated as:

$$TV = \tfrac{1}{2} \times a \times b^2$$

wherein a and b respectively represents length and width.
(2) Relative tumor volume (RTV) is calculated as:

$$RTV = TV_t/TV_0$$

wherein $TV_0$ is the tumor volume when administrated according to different cages ($d_0$) and $TV_t$ is the tumor volume measured each time.
(3) Relative tumor reproduction rate T/C (%) is calculated as follows:

$$T/C(\%) = \frac{T_{RTV}}{C_{RTV}} \times 100$$

$T_{RTV}$: RTV in the treatment group; $C_{RTV}$: RTV in the negative control group. The test results used relative tumor reproduction rate T/C (%) as evaluating indicator of anti-tumor activity.

[Screening results] There was no mortality for the animals in the group of compounds and Sorafenib in the experiments with less toxicity.

TABLE 35

Relative tumor reproduction rate of compounds and Sorafenib on human liver cancer cell bel-7402 transplantation tumor model in nude mice T/C (%)
Relative tumor reproduction rate of compounds 1-10 and Sorafenib on human liver cancer cell bel-7402 transplantation tumor model in nude mice T/C (%)

| | 1 | 2 | 3 | 4 | 5 | 6 | 7 | 8 | 9 | 10 |
|---|---|---|---|---|---|---|---|---|---|---|
| human liver cancer cell bel-7402 transplantation tumor | 33.7 | 35.4 | 30.1 | 15.3 | 15.7 | 19.5 | 34.2 | 30.6 | 36.8 | 28.1 |

| | 11 | 12 | 13 | 14 | 15 | 16 | 17 | 18 | 19 | 20 |
|---|---|---|---|---|---|---|---|---|---|---|
| human liver cancer cell bel-7402 transplantation tumor | 23.7 | 31.6 | 29.8 | 36.1 | 33.6 | 14.9 | 12.5 | 12.7 | 16.3 | 17.2 |

| | 21 | 22 | 23 | 24 | 25 | 26 | 27 | 28 | 29 | 30 |
|---|---|---|---|---|---|---|---|---|---|---|
| human liver cancer cell bel-7402 transplantation tumor | 16.4 | 15.3 | 17.7 | 16.8 | 29.1 | 36.1 | 29.2 | 17.5 | 16.2 | 16.1 |

| | 31 | 32 | 33 | 34 | 35 | 36 | 37 | 38 | Sorafenib |
|---|---|---|---|---|---|---|---|---|---|
| human liver cancer cell bel-7402 transplantation tumor | 33.4 | 31.4 | 32.7 | 31.5 | 34.5 | 37.9 | 36.3 | 31.5 | 35.9 |

| | Compound A' | Compound B' | Compound C' |
|---|---|---|---|
| human liver cancer cell bel-7402 transplantation tumor | 37.2 | 30.4 | 32.6 |

11. Tumor inhibition rate of medicines on renal carcinoma cell line GCR-1 transplanted tumor model in nude mice

[Test animals] female BALB/cA nude mice, 35-40 days old, with weight of 18-22g. There were 12 mice in the negative conrol group and 6 mice in the treatment group.

[Test method] Take eugenic tumor tissues and cut into about 1.5 mm$^3$, and then incoculate subcutaneously at the right armpit of nude mice under the sterile conditions. The diameter of the transplantable tumor in nude mice was determined with a vernier caliper, and the animals were divided into groups after the tumors were grown to 100-300 mm$^3$. Using the method of measuring the tumor diameter, dynamically observe the antitumor effects of tested materials. The diameter of the tumor was determined three times every week and the mouse weight was weighed at the same time. The dosage of the medicine was 60 mg/kg, 6 times every week for 3 weeks. Sorafenib was oral administrated with dosage of 60 mg/kg, 6 times every week for 3 weeks. Equal amount of normal saline was administrated in the negative control group. Observe for one week after administration.

[Detection Indicators and Calculation Methods]
(1) Tumor volume (TV) is calculated as:

$$TV = \tfrac{1}{2} \times a \times b^2$$

wherein a and b respectively represents length and width.
(2) Relative tumor volume (RTV) is calculated as:

$$RTV = TV_t/TV_0°$$

wherein $TV_0$ is the tumor volume when administrated according to different cages ($d_0$) and $TV_t$ is the tumor volume measured each time.
(3) Relative tumor reproduction rate T/C (%) is calculated as follows:

$$T/C(\%) = \frac{T_{RTV}}{C_{RTV}} \times 100$$

$T_{RTV}$: RTV in the treatment group; $C_{RTV}$: RTV in the negative control group. The test results used relative tumor reproduction rate T/C (%) as evaluating indicator of anti-tumor activity.

[Screening results] There was no mortality for the animals in the group of compounds and Sorafenib in the experiments with less toxicity.

TABLE 36

Relative tumor reproduction rate of compounds and Sorafenib on human renal carcinoma GCR-1 cell transplanted tumor model in nude mice T/C (%)

Relative tumor reproduction rate of compounds 11-20 and Sorafenib on human renal carcinoma GCR-1 cell transplanted tumor model in nude mice T/C (%)

| | 1 | 2 | 3 | 4 | 5 | 6 | 7 | 8 | 9 | 10 |
|---|---|---|---|---|---|---|---|---|---|---|
| human renal carcinoma GCR-1 cell transplanted tumor | 30.5 | 23.2 | 31.3 | 9.6 | 11.2 | 12.5 | 21.2 | 29.1 | 28.3 | 27.1 |

| | 11 | 12 | 13 | 14 | 15 | 16 | 17 | 18 | 19 | 20 |
|---|---|---|---|---|---|---|---|---|---|---|
| human renal carcinoma GCR-1 cell transplanted tumor | 32.1 | 20.5 | 28.3 | 31.1 | 22.5 | 9.9 | 11.1 | 12.3 | 13.2 | 13.1 |

Relative tumor reproduction rate of compounds 21-30 and Sorafenib on human renal carcinoma GCR-1 cell transplanted tumor model in nude mice T/C (%)

| | 21 | 22 | 23 | 24 | 25 | 26 | 27 | 28 | 29 | 30 |
|---|---|---|---|---|---|---|---|---|---|---|
| human renal carcinoma GCR-1 cell transplanted tumor | 7.8 | 8.1 | 9.1 | 10.8 | 31.2 | 24.2 | 26.2 | 11.4 | 12.8 | 10.2 |

| | 31 | 32 | 33 | 34 | 35 | 36 | 37 | 38 | Sorafenib |
|---|---|---|---|---|---|---|---|---|---|
| human renal carcinoma GCR-1 cell transplanted tumor | 31.4 | 32.5 | 33.4 | 36.1 | 32.3 | 25.9 | 32.3 | 20.5 | 33.9 |

| | Compound A' | | Compound B' | | Compound C' |
|---|---|---|---|---|---|
| human renal carcinoma GCR-1 cell transplanted tumor | 34.2 | 30.4 | 35.6 | 34.2 | 30.4 |

According to the experimental results, the compound added with specific substituents in A ring have stronger anti-tumor activity than the compouns with no substituent or only amino formyl in A ring, especially the 4#-6# 16#-18# 19#-24# 28#-30# compounds have stonger anti-tumor activity which are stonger than the positive conrol Sorafenib, which have particularly evident effects on the tumor cell metastasis and tumor angiogenesis that are significantly stronger than Sorafenib. The test on normal human umbilical vein endothelial cells CCK8 found that these compounds have less toxicity to normal human cells like endothelial cells, which are relatively safe and reliable, but these compounds can achieve the antitumor activity through inhibiting the tumor angiogenesis. The in vivo transplantation experiments in nude mice showed that 4#-6# 16#-18# 19#-24# 28#-30# compounds have inhibition effects on human liver cancer and renal caner and their effects are better than Sorafenib, but these compounds have very significant effects on lung cancer and the effects obviously exceed the positive control medicine Sorafenib, which is an unexpected result.

The above results indicate that the compounds added with specific substituents in A-ring have more advantages than previously found compounds with no substituent or only amino formyl in A ring, and these new compounds have broader prospects in the treatment of cancer.

What is claimed is:

1. A compound or pharmaceutically acceptable salt thereof, wherein the compound is represented by the following formula [2]

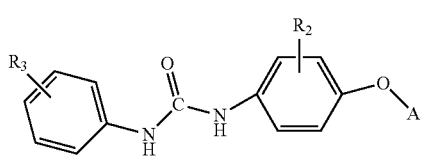

[2]

wherein,
A is monosubstituted quinoline, isoquinoline, quinazoline or pyrrole, and a substituent is halogen, $C_{1-5}$alkyl, $C_{1-5}$haloalkyl, $C_{1-5}$alkoxy, $C_{1-5}$haloalkoxy, amino or nitryl;
$R_2$ is one selected from hydrogen, halogen, alkyl, alkoxy, haloalkyl or haloalkoxy; and
$R_3$ is one or more selected from halogen, alkyl, alkoxy, haloalkyl or haloalkoxy.

2. The compound or pharmaceutically acceptable salt thereof according to claim 1, wherein A is monosubstituted quinazoline, pyrrole or pyrimidine, and a substituent is $C_{1-5}$alkyl, $C_{1-5}$haloalkyl, $C_{1-5}$alkoxy, $C_{1-5}$haloalkoxy, $C_{1-5}$alkylamino, $C_{1-5}$haloalkylamino, amino or nitryl.

3. The compound or pharmaceutically acceptable salt thereof according to claim 2, wherein A is monosubstituted quinazoline, and a substituent is halogen, $C_{1-5}$alkyl, $C_{1-5}$haloalkyl, $C_{1-5}$alkoxy, $C_{1-5}$haloalkoxy, $C_{1-5}$alkylamino, $C_{1-5}$haloalkylamino, amino or nitryl.

4. The compound or pharmaceutically acceptable salt thereof according to claim 1, wherein $R_2$ is one or more selected from hydrogen, halogen, $C_{1-5}$alkyl, $C_{1-5}$alkoxy or $C_{1-5}$haloalkyl.

5. The compound or pharmaceutically acceptable salte thereof according to claim 4, wherein $R_2$ is one or more selected from H, Cl, Br, F, methoxy, ethoxy, propoxy, methyl, ethyl, propyl, isopropyl, butyl, t-butyl or trifluoromethyl.

6. The compound or pharmaceutically acceptable salt thereof according to claim 1, wherein $R_3$ is one or more selected from halogen, $C_{1-5}$ alkyl, $C_{1-5}$ alkoxy, or $C_{1-5}$ haloalkyl.

7. The compound or pharmaceutically acceptable salt thereof according to claim 6, wherein $R_3$ is one or more selected from Cl, Br, F, methoxy, ethoxy, propoxy, methyl, ethyl, propyl, isopropyl, butyl, t-butyl or trifluoromethyl.

8. The compound or pharmaceutically acceptable salt thereof according to claim 1, wherein the salt is selected from:
a) basic salts of inorganic acids and organic acids selected from the group consisting of hydrochloric acid, hydrobromic acid, sulfuric acid, phosphoric acid, mesylate acid, trifluoromethanesulfonic acid, benzene sulfonic acid, paratoluenesulfonic acid, 1-naphthalene sulfonic acid, 2-naphthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid or almonds acid;
b) acid salts of organic and inorganic base, wherein a cation is selected from alkali metal cation, alkaline earth metal cation, ammonium cation, aliphatic-substituted ammonium cation or aromatic-substituted ammonium cation.

9. The compound or pharmaceutically acceptable salt thereof according to any one of claims 1 to 8, wherein the compound is selected from:
the following N'-(4-(4-(6-methoxyquinolinyl)oxy)phenyl) urea
N-(4-chloro-3-(trifluoromethyl)phenyl)-N'-(4-(4-(6-methoxyquinolinyl)oxy)phenyl)urea;
N-(4-fluoro-3-(trifluoromethyl)phenyl)-N'-(4-(4-(6-methoxyquinolinyl)oxy)phenyl)urea;
N-(4-bromo-3-(trifluoromethyl)phenyl)-N'-(4-(4-(6-methoxyquinolinyl)oxy)phenyl)urea;
the following N'-(4-(4-(7-fluoroquinazolinyl)oxy)phenyl) urea
N-(4-chloro-3-(trifluoromethyl)phenyl)-N'-(4-(4-(7-fluoroquinazolinyl)oxy)phenyl)urea;
N-(4-fluoro-3-(trifluoromethyl)phenyl)-N'-(4-(4-(7-fluoroquinazolinyl)oxy)phenyl)urea;
N-(4-bromo-3-(trifluoromethyl)phenyl)-N'-(4-(4-(7-fluoroquinazolinyl)oxy)phenyl)urea;
the following N'-(4-(4-(7-amino-isoquinolyl)oxy)phenyl) urea
N-(4-chloro-3-(trifluoromethyl)phenyl)-N'-(4-(4-(7-amino-isoquinolyl)oxy)phenyl)urea;
N-(4-fluoro-3-(trifluoromethyl)phenyl)-N'-(4-(4-(7-amino-isoquinolyl)oxy)phenyl)urea;
N-(4-bromo-3-(trifluoromethyl)phenyl)-N'-(4-(4-(7-amino-isoquinolyl)oxy)phenyl)urea;
the following N'-(4-(4-(2-methyl-pyrryl)oxy))phenyl)urea
N-(4-chloro-3-(trifluoromethyl)phenyl)-N'-(4-(4-(2-methyl-pyrryl)oxy))phenyl)urea;
N-(4-fluoro-3-(trifluoromethyl)phenyl)-N'-(4-(4-(2-methyl-pyrryl)oxy))phenyl)urea;
N-(4-bromo-3-(trifluoromethyl)phenyl)-N'-(4-(4-(2-methyl-pyrryl)oxy))phenyl)urea.

10. A method of treating colon cancer, sarcoma, lung cancer, liver cancer or renal cancer in subject, the method comprising administering the subject an effective dosage amount of the compound or pharmaceutically acceptable salts thereof according to any one of claim 1 to 8.

* * * * *